(12) United States Patent
Vallera et al.

(10) Patent No.: US 9,371,386 B2
(45) Date of Patent: Jun. 21, 2016

(54) METHODS AND COMPOSITIONS FOR BI-SPECIFIC TARGETING OF CD19/CD22

(76) Inventors: Daniel A. Vallera, Minneapolis, MN (US); Jeff Lion, Fresno, CA (US)

(*) Notice: Subject to any disclaimer, the term of this patent is extended or adjusted under 35 U.S.C. 154(b) by 1243 days.

(21) Appl. No.: 13/256,812

(22) PCT Filed: Mar. 11, 2010

(86) PCT No.: PCT/US2010/027012
§ 371 (c)(1),
(2), (4) Date: Jan. 27, 2012

(87) PCT Pub. No.: WO2010/107658
PCT Pub. Date: Sep. 23, 2010

(65) Prior Publication Data
US 2012/0121614 A1    May 17, 2012

Related U.S. Application Data

(60) Provisional application No. 61/160,530, filed on Mar. 16, 2009.

(51) Int. Cl.
| | |
|---|---|
| A61K 39/395 | (2006.01) |
| C07K 16/28 | (2006.01) |
| A61K 38/16 | (2006.01) |
| A61K 38/19 | (2006.01) |
| A61K 47/48 | (2006.01) |
| A61K 39/00 | (2006.01) |

(52) U.S. Cl.
CPC .......... *C07K 16/2803* (2013.01); *A61K 38/164* (2013.01); *A61K 38/19* (2013.01); *A61K 47/48476* (2013.01); *A61K 47/48561* (2013.01); *A61K 47/48569* (2013.01); *A61K 2039/505* (2013.01); *C07K 2317/565* (2013.01); *C07K 2317/73* (2013.01); *C07K 2319/55* (2013.01)

(58) Field of Classification Search
None
See application file for complete search history.

(56) References Cited

U.S. PATENT DOCUMENTS

| | | | |
|---|---|---|---|
| 5,091,513 A | 2/1992 | Huston et al. | |
| 5,401,511 A | 3/1995 | Margalit | |
| 5,603,872 A | 2/1997 | Margalit | |
| 5,889,155 A | 3/1999 | Ashkenazi et al. | |
| 7,612,181 B2 * | 11/2009 | Wu et al. | 530/387.3 |
| 2005/0214860 A1 | 9/2005 | Zhu et al. | |

FOREIGN PATENT DOCUMENTS

| WO | WO 88/09344 | 12/1988 |
|---|---|---|
| WO | WO 2005/056603 | 6/2005 |

OTHER PUBLICATIONS

Vallera et al. (Clin. Cancer Res., 2005, vol. 11, No. 10, pp. 3879-3888).*
Vallera et al. (Clin. Cancer Res., 2005, vol. 11, No. 10, pp. 3879-3888.*
Vallera et al. (Leukemia Research, Mar. 2005, vol. 29, No. 3, pp. 331-341.*
Alderson et al., "CAT-8015: a second-generation pseudomonas exotoxin A-based immunotherapy targeting CD22-expressing hematologic malignancies", *Clin. Cancer Res.*, 15(3):832-9, 2009.
Herrera et al., "Treatment of SCID/human B cell precursor ALL with anti-CD19 and anti-CD22 immunotoxins", *Leukemia*, 17:334-8, 2003.
Ho et al., "In vitro antibody evolution targeting germline hot spots to increase activity of an anti-CD22 immtmotoxin", *J. Biol Chem.*, 280(1):607-617, 2005.
Hu, et al., "Minibody: A novel engineered anti-carcinoembryonic antigen antibody fragment (single-chain Fv-CH3) which exhibits rapid, high-level targeting of xenografts", *Cancer Res.*, 56:3055-3061, 1996.
Messmann et al., "A phase I study of combination therapy with immunotoxins IgG-HD37-deglycosylated ricin A chain (dgA) and IgG-RFB4-dgA (Combotox) in patients with refractory CD19(+), CD22(+) B cell lymphoma", *Clin. Cancer Res.*, 6:1302-13, 2000.
Onda et al., "An immunotoxin with greatly reduced immunogenicity by identification and removal of B cell epitopes", *Proc. Natl. Acad. Sci. USA.*, 105(32):11311-6, 2008.
PCT International Preliminary Report on Patentability issued in International Application No. PCT/US2010/027012, dated Sep. 20, 2011.
PCT Intertational Search Report and Written Opinion issued in International Application No. PCT/US2010/027012, mailed Oct. 4, 2010.
Vallera et al., "A bispecific recombinant immunotoxin, DT2219, targeting human CD19 and CD22 receptors in an mouse xenograft model of B-cell leukemia/lymphoma", *Clin Cancer Res.*, 11(10):3878-3888, 2005.
Vallera et al., "Genetic alteration of a bispecific ligand-directed toxin targeting human CD19 and CD22 receptors resulting in improved efficacy agonist systemic B cell malignancy", *Leukemia Research*, 33(9):1233-1242, 2009.
Vallera et al., "Molecular modification of a recombinant, bivalent anti-human CD3 immunotoxin (Bic3) results in reduced in vivo toxicity in mice", *Leukemia Research*, 29(3):331-341, 2005.

* cited by examiner

*Primary Examiner* — Laura B Goddard
*Assistant Examiner* — Meera Natarajan
(74) *Attorney, Agent, or Firm* — DLA Piper LLP (US)

(57) ABSTRACT

Methods and composition involving genetically engineered targeting conjugates with reversed orientation of VL and VH chains are provided. For example, in certain aspects targeting conjugates comprising VL and VH chains of anti-CD22 and anti-CD19 are described. In a further aspect, the invention provides methods and targeting conjugates comprising therapeutic agents or diagnostic agents for delivery to B cells.

13 Claims, 13 Drawing Sheets

1.) [DT390]—EASGGPE—[V_H][V_L][hma][V_H][V_L]
   CD22sFv         CD19sFv

2.) [DT390]—EASGGPE—[V_H][V_L][G_4S][V_H][ARL][V_L]
   CD22sFv         CD19sFv

3.) [DT390]—EASGGPE—[V_L][ARL][V_H][G_4S][V_L][ARL][V_H]
   Toxin            CD22sFv         CD19sFv

FIG. 1A 95 kDa —

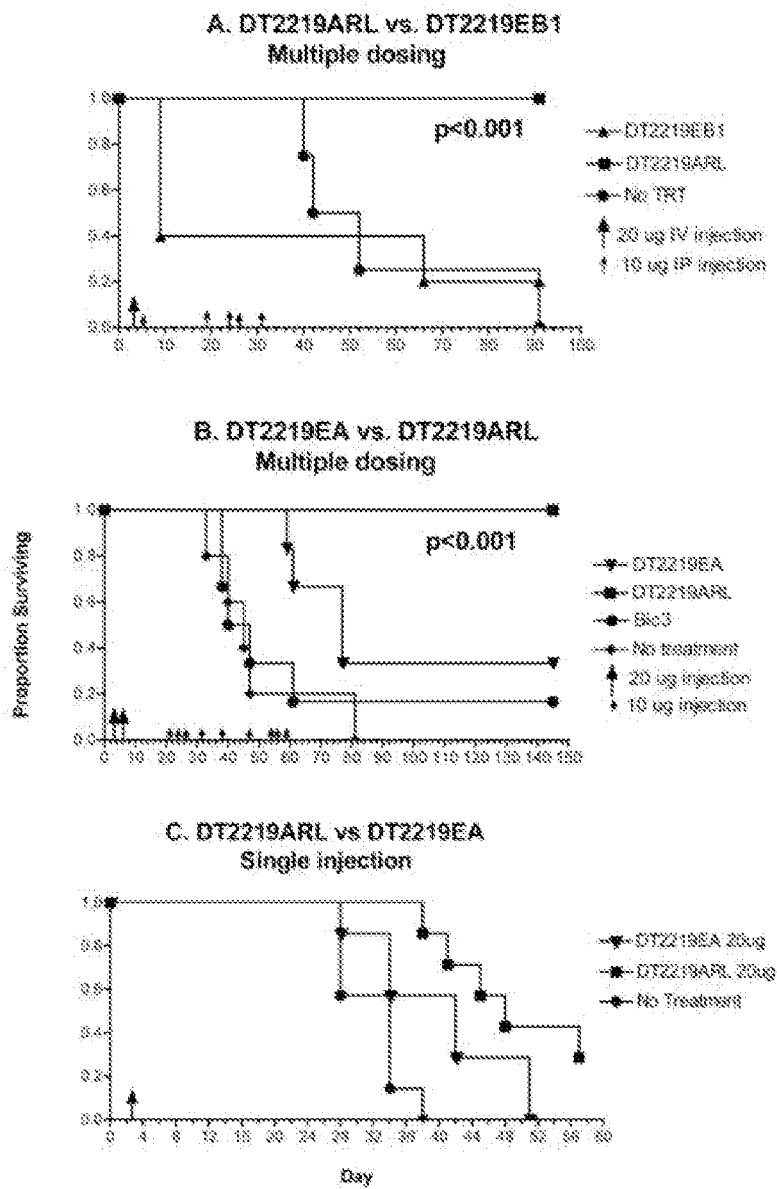
FIGs. 5A-C

METHODS AND COMPOSITIONS FOR BI-SPECIFIC TARGETING OF CD19/CD22

This application is a national phase application under 35 U.S.C. §371 of International Application No. PCT/US2010/027012 filed Mar. 11, 2010, which claims priority to U.S. Provisional Application No. 61/160,530 filed on Mar. 16, 2009, the entire disclosure of which is specifically incorporated herein by reference in its entirety without disclaimer.

This invention was made with government support under grant number R01-CA36725 and R01-CA082154 awarded by the National Institute of Health. The government has certain rights in the invention.

BACKGROUND OF THE INVENTION

1. Field of the Invention

The present invention relates generally to the field of immunology and tumor biology. More particularly, it concerns compositions and methods involving bispecific antibodies for B-cell malignancy therapeutics and/or diagnostics.

2. Description of Related Art

The immune system of vertebrates consists of a number of organs and cell types which have evolved to accurately recognize foreign antigens, specifically bind to, and eliminate/destroy such foreign antigens. Lymphocytes, among other cell types, are critical to the immune system. Lymphocytes are divided into two major sub-populations, T cells and B cells. Although inter-dependent, T cells are largely responsible for cell-mediated immunity and B cells are largely responsible for antibody production (humoral immunity).

In humans, each B cell can produce an enormous number of antibody molecules. Such antibody production typically ceases (or substantially decreases) when a foreign antigen has been neutralized. Occasionally, however, proliferation of a particular B cell will continue unabated and may result in a cancer known as a B cell lymphoma. B-cell lymphomas, such as the B-cell subtype of non-Hodgkin's lymphoma, are significant contributors to cancer mortality. The response of B-cell malignancies to various forms of treatment is mixed. For example, in cases in which adequate clinical staging of non-Hodgkin's lymphoma is possible, field radiation therapy can provide satisfactory treatment. Still, about one-half of the patients die from the disease (Devesa et al., 1987).

Acute leukemia is the most common childhood malignancy, representing 30% of all cancer in American children under the age of 15-19 years and 12% of cancer cases in those aged 15 to 19 years old. In the United States, approximately 2500 new cases are diagnosed annually; 80% of these are B lineage acute lymphoblastic leukemia (B-ALL). Chemotherapy resistant blasts are a frequent cause of treatment failure in all leukemia patients (List, 1996) and alternative therapies are urgently needed.

The majority of chronic lymphocytic leukemias are of the B-cell lineage (Freedman, 1990). This type of B-cell malignancy is the most common leukemia in the Western world (Goodman et al., 1996). The natural history of chronic lymphocytic leukemia falls into several phases. In the early phase, chronic lymphocytic leukemia is an indolent disease, characterized by the accumulation of small mature functionally-incompetent malignant B cells having a lengthened life span. Eventually, the doubling time of the malignant B cells decreases and patients become increasingly symptomatic. While treatment can provide symptomatic relief, the overall survival of the patients is only minimally affected. The late stages of chronic lymphocytic leukemia are characterized by significant anemia and/or thrombocytopenia. At this point, the median survival is less than two years (Foon et al., 1990). Due to the very low rate of cellular proliferation, chronic lymphocytic leukemia is resistant to cytotoxic drug treatment.

Traditional methods of treating B-cell malignancies, including chemotherapy and radiotherapy, have limited utility due to toxic side effects. Therefore, there remains a need to develop novel treatments for B-cell malignancies with improved efficacy.

SUMMARY OF THE INVENTION

The present invention is based in part on the finding that the superior in vivo activity of a conjugate in treating B-cell malignancy results from genetic alterations of antibody or fragments thereof comprised in the conjugate, such as reverse orienting VH-VL domains and adding aggregation reducing/stabilizing linkers.

Thus, in accordance with certain aspects of the present invention, there is provided a conjugate comprising a therapeutic agent conjugated to a targeting moiety comprising at least a first antigen-binding fragment that binds a first antigen and a second antigen-binding fragment that binds a second antigen, wherein the first antigen-binding fragment comprises a first VL domain which is linked at its carboxy terminus to a first VH domain (VL-VH orientation), and/or the second antigen-binding fragment comprises a second VL domain which is linked at its carboxy terminus to a second VH domain (VL-VH orientation). Preferably, the conjugate is further defined as a fusion protein, for example, DT2219ARL having an amino acid sequence of SEQ ID NO:01. The therapeutic agent and targeting moiety may also be chemically conjugated. In certain further embodiments, the antigen-binding fragments may be a full-length antibody, a Fv fragment, or an scFv fragment.

In some further aspects, the therapeutic agent comprises a therapeutic peptide, wherein the therapeutic peptide may be linked at its carboxy or amino terminus to the first or second antigen-binding fragment. In still further embodiments of the invention, the first antigen-binding fragment may be linked at its carboxy terminus to the therapeutic agent or the second antigen-binding fragment, or the second antigen-binding fragment may be linked at its carboxy terminus to the therapeutic agent or the first antigen-binding fragment.

The reversed orientation of variable regions may cause the conjugate to more easily permeate tumor cell or tissue and be more uniformly distributed to contribute to its greater anti-tumor activity. Therefore, at least an antigen-binding fragment (e.g., sFv) with a VL-VH orientation may also have improved therapeutic efficacy. Based on the general description above, the conjugate may have at least 18 variations if the first and second antigen binding fragment are different antigen binding fragments, such as anti-CD19 and ant-CD22 scFvs. For example, following the conventional order from N terminus to C terminus, the therapeutic peptide may be followed by six potential arrangements of two scFvs: (1) the VL and VH regions of anti-CD22 and the VL and VH regions of anti-CD19, (2) the VL and VH regions of anti-CD22 and the VH and VL regions of anti-CD19, (3) the VH and VL regions of anti-CD22 and the VL and VH regions of anti-CD19, (4) the VL and VH regions of anti-CD19 and the VL and VH regions of anti-CD22, (5) the VL and VH regions of anti-CD19 and the VH and VL regions of anti-CD22, or (6) the VH and VL regions of anti-CD19 and the VL and VH regions of anti-CD22. Alternatively, the therapeutic peptide may be in the C terminus and preceded by the six possible combinations of VL and VH regions of two scFvs as described above, or may be in the middle between two scFvs with another six possibilities. In certain aspects, the conjugate may also be monospecific or multispecific of recognizing more than two targets with a least a VL-VH structure to improve penetration and efficacy.

To treat B-cell malignancy, the first or second antigen may be any B cell surface marker known in the art, such as CD19, CD22, CD45, CD10, CD5, CD79a, or polymorphic HLA-DR. Furthermore, in highly preferred aspects of the invention, the first antigen and second antigen may be different for bispecificity, for example, the first antigen is CD19, and the second antigen is CD22. Dual antigen targeting may be more potent and superior and less toxic compared with the sum of single targeting.

Regarding design of the conjugate as a fusion protein, optimal linkers between different domains may contribute to improved yield and refolding. In certain aspects of the invention, the linker connecting the first VL domain to the first VH domain or connecting the second VL domain to the second VH domain may be a peptide linker, preferably comprising at least three charged resides selected from the group consisting of lysine, arginine, glutamic acid, aspartic acid, and histidine, which may improve refolding and help increase protein yield. A particular example may be an ARL linker (SEQ ID NO:02). The first antigen-binding fragment may be linked to the second antigen-binding fragment via a third peptide linker, such as a G4S linker.

Therapeutic agents are known in the art and may be used in the methods and compositions of the invention. For example, in some aspects, the therapeutic agent is a cytotoxic agent, a cytokine, an anti-angiogenic agent, a chemotherapeutic agent, a pro-apoptosis agent, an enzyme, a hormone, a growth factor, a peptide, a protein, an antibiotic, an antibody, a Fab fragment of an antibody, an antigen, a survival factor, an anti-apoptotic agent, a hormone antagonist, a virus, a bacteriophage, a bacterium, a liposome, a cell, a nucleic acid or an expression vector. Preferably, the agent is a cytotoxic agent, which may comprise a peptide, a polypeptide, or a small molecule, such as gelonin, ricin, abrin, diphtheria toxin, *Pseudomonas* exotoxin, *Clostridium perfringens* enterotoxin, dodecandrin, tricosanthin, tricokirin, bryodin, mirabilis antiviral protein, barley ribosome-inactivating protein (BRIP), pokeweed antiviral protein (PAPs), saporin, luffin, momordin, colicin, anthrax toxin, tetanus toxin, botulinum neurotoxin, and fragments thereof. For example, the cytotoxic agent comprises diphtheria toxin, the translocation enhancer region of diphtheria toxin, or the amino terminal 390 amino acids of diphtheria toxin. In another aspect, the cytotoxic agent may comprise *Pseudomonas* exotoxin KDEL (SEQ ID NO:05) or *Pseudomonas* exotoxin KDEL7 mutant (7mut).

The skilled artisan will understand that the agent may be an anti-angiogenic agent which includes, but not is not limited to, thrombospondin, angiostatin, endostatin or pigment epithelium-derived factor, angiotensin, laminin peptides, fibronectin peptides, plasminogen activator inhibitors, tissue metalloproteinase inhibitors, interferons, interleukin 12, platelet factor 4, IP-10, Gro-β, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, paclitaxel, accutin, cidofovir, vincristine, bleomycin, AGM-1470, platelet factor 4 or minocycline. In a further aspect, the agent may be a cytokine such as interleukin 1 (IL-1), IL-2, IL-5, IL-10, IL-11, IL-12, IL-18, interferon-γ (IF-γ), IF-α, IF-β, tumor necrosis factor-α (TNF-α), or GM-CSF (granulocyte macrophage colony stimulating factor).

For therapeutic purpose, the conjugate may be further defined as being comprised in a pharmaceutically acceptable carrier. There may also be provided a pharmaceutical composition comprising the conjugate for its superior therapeutic activity, a nucleic acid molecule comprising a sequence encoding the fusion protein defining the conjugate and an expression vector comprising the nucleic acid for various purposes.

Additional aspects of the invention concern methods of treating a human patient having a B-cell malignancy, comprising the step of administering to the patient with the conjugates or the compositions of the present invention. For example, the B-cell malignancy may be B-cell subtype of non-Hodgkin's lymphoma, Burkitt's lymphoma, multiple myeloma, acute lymphoblastic leukemia (ALL), chronic lymphocytic leukemia (CLL), chronic myelogenous leukemia (CML), hairy cell leukemia, or prolymphocytic leukemia.

By targeting tumor cells specifically or preferentially, the conjugate may exert an anti-tumor activity, such as increasing tumor-free survival, killing a tumor cell or tissue, inducing apoptosis of a tumor cell or tissue, inhibiting tumor growth, inhibiting metastatic spread, reducing tumor burden and inducing tumor regression. To have a better anti-tumor effect, the conjugate may be used to treat a patient in combination with chemotherapy, radiotherapy, surgery, hormone therapy or gene therapy.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B. Construction of DT2219 variants. FIG. 1A. Construction of DT2219ARL. (1) The original DT2219EA construct consisting of the first 389 amino acids of the DT ($DT_{390}$), the $V_H$ and $V_L$ regions of anti-CD22 (sFv) and anti-CD19 (Dorken et al., 1983) linked by a 20 amino acid segment of human muscle aldolase (hma). (2) To construct DT2219ARL, the $V_H$-$V_L$ orientation was reversed and the $V_L$ and $V_H$ genes of each sFv were conjoined by a fragment encoding the ARL linker. (3) The final target gene was spliced into pET21d vector. FIG. 1B. SDS-PAGE gel containing all 3 DT2219 variants used in these studies. Lane 1 and 8: Molecular weight standards, Lane 2: 95 kDa DT2219ARL, Lane 3: DT2219EA, Lane 4: DT2219EB1, Lane 5: RFB4 monoclonal antibody, Lane 6: HD37 monoclonal antibody, Lane 7: $DT_{390}$ (partially purified). The gel was stained using Coomassie blue and shows size and purity of the agents.

FIG. 2A. Daudi cells were cultured with fusion proteins and proliferation was measured by uptake of tritiated thymidine. Data are percentage of control response where control response is untreated cells. Data are expressed as mean±standard deviation (SD). The mean values of untreated Daudi cells were 121,001±8,276 cpm/20,000 cells. FIG. 2B. Selectivity was determined on the CD19⁻CD22⁻ HPBMLT cell line in a separate experiment. The mean cpm of untreated HPBMLT in this experiment was 61,993±7,178 cpm/20,000 cells. DT2219ARL differed significantly from the control Bic3 group at 0.01-100 nM by Student t-test ($p<0.0001$). FIG. 2C. In a third experiment, the ability of the ligands themselves to mediate cytotoxicity was tested by inactivating the diphtheria toxin with the DT2219GE mutation that disrupts toxin activity and leaves the ligands intact. The mean cpm of untreated Daudi in this experiment was 112,164±10,379 cpm/20,000 cells. FIG. 2D. The anti-proliferative effect of DT2219ARL, DT22, DTIL19, and a mixture of DT22/DT19 on Daudi cells was tested by measuring ³H-thymidine uptake 72 hours following IT exposure. Points on each graph represent mean of triplicate samples±SD. Control counts=61, 993±7,178 cpm/20,000 cells.

FIGS. 5A-C. Groups of SCID (Severe Combined Immunodeficiency) mice were given $10^6$ Daudi cells IV to induce systemic disease. FIG. 5A. Three days following Daudi injection, mice were given the exact same injection schedule of multiple intraperitoneal (ip) injections of DT2219ARL and DT2219EB1 in order to compare them to no treatment controls. Data were graphed as proportion surviving versus time. Statistical analysis was performed using the Log-Rank test and the DT2219ARL group significantly differed from the no treatment group ($p<0.001$). FIG. 5B. Three days following Daudi injection, mice were given ip treatment with DT2219EA and DT2219ARL in comparison to no treatment controls and to Bic3 immunotoxin control treated mice. The DT2219ARL group significantly differed from the DT2219EA group, the Bic3 group, and the no treatment group ($p<0.001$). FIG. 5C. Three days following Daudi injection, mice were given a single ip injection of DT2219EA and DT2219ARL in comparison to no treatment controls. Only the DT2219ARL group significantly differed from the no treatment group.

FIG. 6A. Mice were either treated with DT2219ARL (M1, M2, M3, and M4) on days 3, 5, 11, 16, and 18 or untreated (M5, M6, M7, and M8). Luciferase bioluminescence was measured as photons/s/cm²/sr. FIG. 6B. The same data as shown in FIG. 6A are graphed in FIG. 6B. Data are expressed as total activity graphed over time for each individual animal (M1-M8). FIG. 6C. Digital images of illustrating tumor progression in untreated Raji-luc mice. Bioluminescent imaging is shown for 3 untreated mice M9-M11 on day 21. Because the Raji-luc line has a GFP reporter gene as well as a luciferase reporter gene, fluorescent imaging is also shown for animals M9, M10, and M11. Lymphoma can be seen in lung, bone marrow, lymph node and compressing the spinal chord which likely causes hind limb paralysis (HLP). GFP imaging correlates with luciferase imaging.

FIG. 7A. Average weight of two rabbits. FIG. 7B. ALT enzyme levels from the same rabbits. FIG. 7C. Frozen liver section from a rabbit treated with 500 μg/kg DT2219ARL. The section was stained with H and E and is shown at 100× magnification.

DESCRIPTION OF ILLUSTRATIVE EMBODIMENTS

I. The Present Invention

Figure 2A:
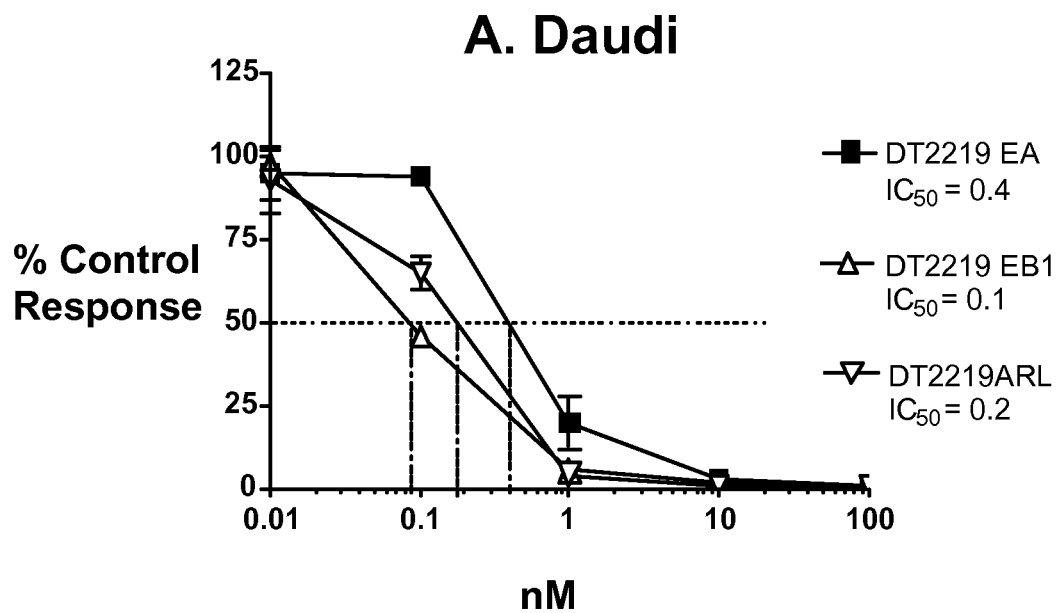
FIGS. 2A-D. The in vitro effect of the DT2219 mutant proteins.

Certain aspects of the instant invention provide improved immunoconjugates and methods for treating B-cell malignancy by genetic engineering of variable domain orientations. For example, a bispecific ligand-directed toxin recognizing CD19 and CD22 resulted in surprisingly long-term tumor-free survival in well established animal models. Further embodiments and advantages of the invention are described below.

II. Conjugates

Compositions and methods of the present invention involve genetically engineered targeting conjugates comprising at least a VL-VH structure. The conjugates may comprise a targeting moiety and a therapeutic agent, which may be chemically conjugated, crosslinked, or fused at the protein level using conventional methods.

Particularly, the conjugate may be an immunotoxin. Immunotoxins (IT) are synthesized by coupling an antibody or antigen-binding fragment to a toxin, particularly a potent, catalytic toxin, such as diphtheria toxin, capable of inhibiting protein synthesis (Kreitman, 2002). Catalytic toxins are preferable because one molecule entering the cytosol can kill a cell.

In certain aspects, bispecific ligand-directed toxins (BLTs) are contemplated. BLTs are novel single-chain biologicals synthesized by linking a truncated toxin to two well-established targeting ligands with the goal of increasing targeting capability. For successful BLT, the final construct may have better anti-tumor activity than its monospecific counterparts or a mixture of the two, thus indicating an advantage of including both ligands on the same single-chain molecule (Stish et al., 2007a; Vallera et al., 2008; Stish et al., 2008; Stish et al., 2007b; Todhunter et al., 2004). For example, DT2219ARL fulfilled these criteria for a successful BLT.

A. Fusion Proteins

Certain embodiments of the present invention concern fusion proteins. These molecules generally have all or a substantial portion of a targeting peptide, linked at the N- or C-terminus, to all or a portion of a second therapeutic polypeptide or protein. For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. In preferred embodiments, the fusion proteins of the instant invention comprise a targeting peptide with a VL-VH oriented antigen binding fragment linked to a therapeutic protein or peptide.

Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated that within the scope of the present invention virtually any protein or peptide could be incorporated into a fusion protein comprising a targeting peptide.

Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

B. Linkers

Bifunctional cross-linking reagents have been extensively used for a variety of purposes including preparation of affinity matrices, modification and stabilization of diverse structures, identification of ligand and receptor binding sites, and structural studies. Suitable peptide linkers may be used to link the therapeutic agent to the targeting moiety in the present invention, such as an ARL linker used to link VL to VH in the antigen-binding fragments.

Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied.

A majority of heterobifunctional cross-linking reagents contains a primary amine-reactive group and a thiol-reactive group. In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups.

If desired, the targeting moiety and the therapeutic agent may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metallaproteinase, such as collagenase, gelatinase, or stromelysin.

Amino acids such as selectively-cleavable linkers, synthetic linkers, or other amino acid sequences may be used to separate a targeting moiety or peptide from another peptide, adjuvant or a therapeutic compound.

Additionally, while numerous types of disulfide-bond containing linkers are known that can successfully be employed to conjugate the toxin moiety with the targeting agent, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the toxin moiety prior to binding at the site of action. It can be considered as a general guideline that any biochemical cross-linker that is appropriate for use in an immunotoxin will also be of use in the present context, and additional linkers may also be considered.

Exemplary methods for cross-linking ligands to liposomes are described in U.S. Pat. No. 5,603,872 and U.S. Pat. No. 5,401,511, each specifically incorporated herein by reference in its entirety). Various ligands can be covalently bound to liposomal surfaces through the cross-linking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites are dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl)carbodiimide (EDC). Through the complex chemistry of cross-linking, linkage of the amine residues of the recognizing substance and liposomes is established.

Once conjugated, the peptide generally will be purified to separate the conjugate from unconjugated targeting agents or coagulants and from other contaminants. A large number of purification techniques are available for use in providing conjugates of a sufficient degree of purity to render them clinically useful.

Purification methods based upon size separation, such as gel filtration, gel permeation or high performance liquid chromatography, will generally be of most use. Other chromatographic techniques, such as Blue-Sepharose separation, may also be used. Conventional methods to purify the fusion proteins from inclusion bodies are particularly useful for the present invention, such as using weak detergents like sodium N-lauroyl-sarcosine (SLS).

In addition to chemical conjugation, a targeting or therapeutic peptide may be modified at the protein level. Included within the scope of the invention are protein fragments or other derivatives or analogs that are differentially modified during or after translation, for example, by glycosylation, acetylation, phosphorylation, amidation, derivatization by known protecting/blocking groups, and proteolytic cleavage. Any number of chemical modifications may be carried out by known techniques, including but not limited to specific chemical cleavage by cyanogen bromide, trypsin, chymotrypsin, papain, V8 protease, $NaBH_4$, acetylation, formylation, farnesylation, oxidation, reduction; metabolic synthesis in the presence of tunicamycin.

C. Targeting Moiety

The targeting moiety may comprise at least one antigen binding fragment, for example, two antigen binding fragments. Specific examples are anti-CD22 and anti-19 scFvs. Other specific cell markers may also be used. Non-limiting examples of B cell surface markers include CD19, CD22, CD45, CD10, CD5, CD79a, and polymorphic HLA-DR.

Examples of antigen binding fragments suitable for the present invention include, without limitation: (i) the Fab fragment, consisting of VL, VH, CL and CH1 domains; (ii) the "Fv" fragment consisting of the VL and VH domains of a single antibody; (iii) F(ab')2 fragments, a bivalent fragment comprising two linked Fab fragments; (iv) single chain Fv molecules ("scFv"), wherein a VH domain and a VL domain are linked by a peptide linker which allows the two domains to associate to form a binding domain; (v) bi-specific single chain Fv dimers (see U.S. Pat. No. 5,091,513) and (vi) diabodies, multivalent or multispecific fragments constructed by gene fusion (US Patent Pub. 2005/0214860). Fv, scFv or diabody molecules may be stabilized by the incorporation of disulphide bridges linking the VH and VL domains. Minibodies comprising a scFv joined to a CH3 domain may also be made (Hu et al., 1996).

"Single-chain Fv," "scFv" or "sFv" antibody fragments comprise the VH and VL domains of antibody, wherein these domains are present in a single polypeptide chain. Generally, the Fv polypeptide further comprises a peptide linker between the VH and VL domains which enables the sFv to form the desired structure for antigen binding. For a review of sFv see The Pharmacology of Monoclonal Antibodies (1994).

CD19, a 95 kDa membrane glycoprotein, is considered by many to be the most ubiquitous marker expressed on B cells. CD19 is expressed not only on mature B cells, but also on late pre-B cells. It is broadly expressed on B cell leukemia/lymphoma (Anderson et al., 1984) including B-ALL. For CD19 targeting, investigators using conventional biochemically linked anti-CD19 IT have reported anti-cancer effects (Goulet et al., 1997; Stone et al., 1996; flavell et al., 1995; Ghetie et al., 1994; Uckun et al., 1986). However, these have not reached the mainstream because of varied degrees of effectiveness.

CD22 or cluster of differentiation-22, is a molecule belonging to the SIGLEC family of lectins. Generally speaking, CD22 is a regulatory molecule that prevents the overactivation of the immune system and the development of autoimmune diseases. CD22 is a sugar binding transmembrane protein, which specifically binds sialic acid with an immunoglobulin (Ig) domain located at its N-terminus. The presence of Ig domains makes CD22 a member of the immunoglobulin superfamily. CD22 functions as an inhibitory receptor for B cell receptor (BCR) signaling.

Anti-CD22 IT have proven successful in the treatment of rare Hairy Cell Leukemia (HCL) (Kreitman et al., 2005). However, HCL represents a narrow sampling of patients with leukemia and expanding the use of the drug to the wider population of patients is critical. In a previous study, the inventors cloned a new molecule by fusing two repeating sFv subunits recognizing human CD19 and human CD22 spliced downstream of truncated DT390 to broaden toxin delivery and anti-leukemia affect (Vallera et al., 2005). Studies targeting these 2 ligands with monomeric conventional immunotoxins showed promise and led to clinical trials (Herrera et al., 2003; Messmann et al., 2000).

The present invention provides a conjugate that may be superior to the known anti-CD19, anti-CD22 immunotoxins or existing bispecific immunotoxins in terms of its novel VL-VH orientation.

III. Therapeutic Agents

In certain embodiments, it may be desirable to couple specific bioactive agents to one or more targeting peptides (particularly CD19 and CD22 dual targeting peptides) for targeted delivery to an organ, tissue or cell type. Such agents include, but are not limited to, cytotoxic molecules, cytokines, chemokines, pro-apoptosis factors and anti-angiogenic factors as well as imaging agents.

A. Cytotoxic Agents

Chemotherapeutic (cytotoxic) agents of potential use include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raioxifene, tamoxifen, taxol, temazolomide (an aqueous form of DTIC), transplatinum, vinblastine and methotrexate, vincristine, or any analog or derivative variant of the foregoing. Most chemotherapeutic agents fall into the categories of alkylating agents, antimetabolites, antitumor antibiotics, corticosteroid hormones, mitotic inhibitors, and nitrosoureas, hormone agents, miscellaneous agents, and any analog or derivative variant thereof.

In addition, there are a variety of protein toxins (cytotoxic proteins), which include a number of different classes, such as those that inhibit protein synthesis: ribosome-inactivating proteins of plant origin, such as ricin, abrin, gelonin, and a number of others, and bacterial toxins such as *pseudomonas* exotoxin and diphtheria toxin.

Particularly, Diphtheria toxin (DT) was chosen as an example for construction due to its irreversible catalytic activity and research demonstrating a single molecule causes cell death (Yamaizumi et al., 1978). Also, it is desirable to have new anti-cancer agents that kill by protein synthesis inhibition, a mechanism entirely different and unrelated to the mechanism of most conventional chemotherapeutic agents. The truncated form of DT (DT390; DT390 protein sequence is SEQ ID NO:03, encoded by SEQ ID NO:04) was used in Examples due to previous research describing a series of internal frame deletion mutations that established amino acid 389 as the best location for genetic fusion of DT to targeting ligands (Williams et al., 1990). DT390 contains the A fragment of native DT that catalyzes ADP ribosylation of elongation factor 2 (EF-2) leading to irreversible inhibition of protein synthesis and cell death (Collier, 1975; Oppenheimer and Bodley, 1981).

Chemotherapeutic agents and methods of administration, dosages, etc. are well known to those of skill in the art (see for example, the "Physicians Desk Reference", Goodman & Gilman's "The Pharmacological Basis of Therapeutics" and in "Remington's Pharmaceutical Sciences" 15$^{th}$ ed., pp 1035-1038 and 1570-1580, incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject. Examples of specific chemotherapeutic agents and dose regimes are also described herein. Of course, all of these dosages and agents described herein are exemplary rather than limiting, and other doses or agents may be used by a skilled artisan for a specific patient or application. Any dosage in-between these points, or range derivable therein is also expected to be of use in the invention.

B. Cytokines and Chemokines

The term "cytokine" is a generic term for proteins released by one cell population that act on another cell as intercellular mediators.

Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-.beta.; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1.alpha., IL-2, IL-3, IL-4, IL-5, IL-6, IL-7, IL-8, IL-9, IL-10, IL-11, IL-12; IL-13, IL-14, IL-15, IL-16, IL-17, IL-18, LIF, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. It may be advantageous to express a particular chemokine gene in combination with, for example, a cytokine gene, to enhance the recruitment of other immune system components to the site of treatment. Chemokines include, but are not limited to, RANTES, MCAF, MIP1-α, MIP1-β, and IP-10. The skilled artisan will recognize that certain cytokines are also known to have chemoattractant effects and could also be classified under the term chemokines.

C. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins that share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

Non-limiting examples of pro-apoptosis agents contemplated within the scope of the present invention include granzyme B, Bax, TNF-α, TNF-β, TNF-like molecule, TGF-β, IL-12, IL-3, IL-24, IL-18, TRAIL, IFN-α, IFN-β, IFN-γ, Bcl-2, Fas ligand, caspases, gramicidin, magainin, mellitin, defensin, cecropin, $(KLAKLAK)_2$ (SEQ ID NO:09), $(KLAKKLA)_2$ (SEQ ID NO:010), $(KAAKKAA)_2$ (SEQ ID NO:11) or $(KLGKKLG)_3$ (SEQ ID NO:12).

D. Angiogenic Inhibitors

In certain embodiments the present invention may concern administration of targeting peptides attached to anti-angiogenic agents, such as angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP470, endostatin, paclitaxel, accutin, angiostatin, cidofovir, vincristine, bleomycin, AGM-1470, platelet factor 4 or minocycline.

Proliferation of tumors cells relies heavily on extensive tumor vascularization, which accompanies cancer progression. Thus, inhibition of new blood vessel formation with anti-angiogenic agents and targeted destruction of existing blood vessels have been introduced as an effective and relatively non-toxic approach to tumor treatment. (Arap et al., 1998; Arap et al., 1998; Ellerby et al., 1999). A variety of anti-angiogenic agents and/or blood vessel inhibitors are known (e.g., Folkman, 1997; Eliceiri and Cheresh, 2001).

E. Imaging Agents and Radioisotopes

In certain embodiments, the claimed targeting peptides or proteins of the present invention may be attached to imaging agents of use for imaging and diagnosis of various diseased organs, tissues or cell types. Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509). Proteins or peptides also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, $^{14}$-carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled proteins or peptides of the present invention may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides according to the invention may be labeled with technetium-$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as $SNCl_2$, a buffer solution such as sodium-potassium phthalate solution, and the peptide. Intermediary functional groups that are often used to bind radioisotopes that exist as metallic ions to peptides are diethylenetriaminepenta-acetic acid (DTPA) and ethylene diaminetetra-acetic acid (EDTA). Also contemplated for use are fluorescent labels, including rhodamine, fluorescein isothiocyanate and renographin.

In certain embodiments, the claimed proteins or peptides may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

F. Alkylating Agents

Alkylating agents are drugs that directly interact with genomic DNA to prevent cells from proliferating. This category of chemotherapeutic drugs represents agents that affect all phases of the cell cycle, that is, they are not phase-specific. An alkylating agent, may include, but is not limited to, a nitrogen mustard, an ethylenimene, a methylmelamine, an alkyl sulfonate, a nitrosourea or a triazines. They include but are not limited to: busulfan, chlorambucil, cisplatin, cyclophosphamide (cytoxan), dacarbazine, ifosfamide, mechlorethamine (mustargen), and melphalan.

G. Antimetabolites

Antimetabolites disrupt DNA and RNA synthesis. Unlike alkylating agents, they specifically influence the cell cycle during S phase. Antimetabolites can be differentiated into various categories, such as folic acid analogs, pyrimidine analogs and purine analogs and related inhibitory compounds. Antimetabolites include but are not limited to, 5-fluorouracil (5-FU), cytarabine (Ara-C), fludarabine, gemcitabine, and methotrexate.

H. Natural Products

Natural products generally refer to compounds originally isolated from a natural source, and identified as having a pharmacological activity. Such compounds, analogs and derivatives thereof may be, isolated from a natural source, chemically synthesized or recombinantly produced by any technique known to those of skill in the art. Natural products include such categories as mitotic inhibitors, antitumor antibiotics, enzymes and biological response modifiers.

Mitotic inhibitors include plant alkaloids and other natural agents that can inhibit either protein synthesis required for cell division or mitosis. They operate during a specific phase during the cell cycle. Mitotic inhibitors include, for example, docetaxel, etoposide (VP16), teniposide, paclitaxel, taxol, vinblastine, vincristine, and vinorelbine.

Taxoids are a class of related compounds isolated from the bark of the ash tree, *Taxus brevifolia*. Taxoids include but are not limited to compounds such as docetaxel and paclitaxel. Paclitaxel binds to tubulin (at a site distinct from that used by the vinca alkaloids) and promotes the assembly of microtubules.

Vinca alkaloids are a type of plant alkaloid identified to have pharmaceutical activity. They include such compounds as vinblastine (VLB) and vincristine.

I. Antibiotics

Certain antibiotics have both antimicrobial and cytotoxic activity. These drugs also interfere with DNA by chemically inhibiting enzymes and mitosis or altering cellular membranes. These agents are not phase specific so they work in all phases of the cell cycle. Examples of cytotoxic antibiotics include, but are not limited to, bleomycin, dactinomycin, daunorubicin, doxorubicin (Adriamycin), plicamycin (mithramycin) and idarubicin.

J. Miscellaneous Agents

Miscellaneous cytotoxic agents that do not fall into the previous categories include, but are not limited to, platinum coordination complexes, anthracenediones, substituted ureas, methyl hydrazine derivatives, amsacrine, L-asparaginase, and tretinoin. Platinum coordination complexes include such compounds as carboplatin and cisplatin (cis-DDP). An exemplary anthracenedione is mitoxantrone. An exemplary substituted urea is hydroxyurea. An exemplary methyl hydrazine derivative is procarbazine (N-methylhydrazine, MIH). These examples are not limiting and it is contemplated that any known cytotoxic, cytostatic or cytocidal agent may be attached to targeting peptides and administered to a targeted organ, tissue or cell type within the scope of the invention.

K. Dosages

The skilled artisan is directed to "Remington's Pharmaceutical Sciences" 15th Edition, chapter 33, and in particular to pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA Office of Biologics Standards.

IV. Proteins and Peptides

In certain embodiments, the present invention concerns novel compositions comprising at least one protein or peptide, such as antigen-binding fragments or therapeutic peptides. These peptides may be comprised in a fusion protein or conjugated to an agent as described supra.

A. Proteins and Peptides

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide are used interchangeably herein.

In certain embodiments the size of at least one protein or peptide may comprise, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown on Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for known genes may be amplified and/or expressed using the techniques disclosed herein or as would be know to those of ordinary skill in the art. Alternatively, various commercial preparations of proteins, polypeptides and peptides are known to those of skill in the art.

B. Protein Purification

In certain embodiments a protein or peptide may be isolated or purified. Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70% about 80%, about 90%, about 95%, or more of the proteins in the composition.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

V. Nucleic Acids

Nucleic acids according to the present invention may encode a targeting peptide, a fusion protein, a therapeutic peptide, or other protein or peptide. The nucleic acid may be derived from genomic DNA, complementary DNA (cDNA) or synthetic DNA. Where incorporation into an expression vector is desired, the nucleic acid may also comprise a natural intron or an intron derived from another gene. Such engineered molecules are sometime referred to as "mini-genes."

A "nucleic acid" as used herein includes single-stranded and double-stranded molecules, as well as DNA, RNA, chemically modified nucleic acids and nucleic acid analogs. It is contemplated that a nucleic acid within the scope of the present invention may be of almost any size, determined in part by the length of the encoded protein or peptide.

It is contemplated that targeting peptides, fusion proteins and therapeutic peptides may be encoded by any nucleic acid sequence that encodes the appropriate amino acid sequence. The design and production of nucleic acids encoding a desired amino acid sequence is well known to those of skill in the art, using standardized codon tables. In preferred embodiments, the codons selected for encoding each amino acid may be modified to optimize expression of the nucleic acid in the host cell of interest. Codon preferences for various species of host cell are well known in the art.

In addition to nucleic acids encoding the desired peptide or protein, the present invention encompasses complementary nucleic acids that hybridize under high stringency conditions with such coding nucleic acid sequences. High stringency conditions for nucleic acid hybridization are well known in the art. For example, conditions may comprise low salt and/or high temperature conditions, such as provided by about 0.02 M to about 0.15 M NaCl at temperatures of about 50 degree to about 70 degree. It is understood that the temperature and ionic strength of a desired stringency are determined in part by the length of the particular nucleic acid(s), the length and nucleotide content of the target sequence(s), the charge composition of the nucleic acid(s), and to the presence or concentration of formamide, tetramethylammonium chloride or other solvent(s) in a hybridization mixture.

VI. B-Cell Malignancy

In certain embodiments, the invention also provides a method of treating a subject with a B-cell malignancy, which comprises administering to the subject an effective amount of the B cell targeting conjugates or compositions described herein. As used herein, "subject" means any animal afflicted with a B cell malignancy. In preferred embodiments, the subject is a human. As used herein, "treating" means either slowing, stopping or reversing the progression of a B cell malignancy. Other clinical parameters may also be used to evaluate efficacy of treatment as are known by the skilled clinician such as increased survival time, inhibition of metastasis, and the like. In preferred embodiments, "treating" means reversing the progression to the point of eliminating the disorder. As used herein, "afflicted with or having a B cell malignancy" means that the subject harbors at least one cancerous cell that expresses B cell markers, including but not limited to CD19 and CD22.

B cells are lymphocytes that play a large role in the humoral immune response (as opposed to the cell-mediated immune response, which is governed by T cells). The principal functions of B cells are to make antibodies against antigens, perform the role of Antigen Presenting Cells (APCs) and eventually develop into memory B cells after activation by antigen interaction. B cells are an essential component of the adaptive immune system.

The term "B-cell malignancy," and grammatical variants thereof, are used in the broadest sense to refer to malignancies or neoplasms of B cells that typically arise in lymphoid tissues, such as bone marrow or lymph nodes, but may also arise in non-lymphoid tissues, such as thyroid, gastrointestinal tract, salivary gland and conjunctiva. The treatment methods of the present invention specifically concern B cell malignancies including, without limitation, B-cell subtype of non-Hodgkin's lymphoma, Burkitt's lymphoma, multiple myeloma, acute lymphoblastic leukemia (ALL), chronic lymphocytic leukemia (CLL), chronic myelogenous leukemia (CML), hairy cell leukemia, and prolymphocytic leukemia.

B-cell type Non-Hodgkin's Lymphoma is a term that is used to encompass a large group (over 29 types) of lymphomas caused by malignant (cancerous) B cell lymphocytes, and represents a large subset of the known types of lymphoma. B-cells are known to undergo many changes in their life cycle dependent on complex intracellular signaling processes, and apparently different types of B-cell malignancies can occur at different stages of the life cycle of B-cells. At the stem cell stage, acute lymphocytic leukemia (ALL) or lymphoblastic lymphoma/leukemia can typically develop. Precursor B-cells can develop precursor B lymphoblastic lymphoma/leukemia. Typical malignancies of immature B-cells include small non-cleaved cell lymphoma and possibly Burkitt's/non-Burkitt's lymphoma. B cells before antigen exposure typically develop chronic lymphocytic leukemia (CLL) or small lymphocytic lymphoma, while after antigen exposure typically follicular lymphomas, large cell lymphoma and immunoblastic lymphoma are observed. There are also classification systems that characterize B-cell lymphomas by the rate of growth distinguishing aggressive (fast growing) and indolent (slow growing) lymphomas. For example, Burkitt's/non-Burkitt's lymphoma and LCL lymphoma belong in the aggressive group, while indolent lymphomas include follicular center cell lymphomas (FCCL), follicular large cell lymphomas, and follicular small cleaved cell lymphomas.

Non-Hodgkin's Lymphomas are also characterized by the stage of development. Stage I: cancer is found in only one lymph node area, or in only one area or organ outside the lymph nodes. Stage II: (1) Cancer is found in two or more lymph node areas on the same side of the diaphragm (the thin muscle under the lungs that helps breathing), or, (2) cancer is found in only one area or organ outside the lymph nodes and in the lymph nodes around it, or (3) other lymph node areas on the same side of the diaphragm may also have cancer. Stage III: Cancer is found in lymph node areas on both sides of the diaphragm. The cancer may also have spread to an area or organ near the lymph node areas and/or to the spleen. Stage IV: (1) Cancer has spread to more than one organ or organs outside the lymph system; cancer cells may or may not be found in the lymph nodes near these organs, or (2) cancer has spread to only one organ outside the lymph system, but lymph nodes far away from that organ are involved.

B-cell chronic lymphocytic leukemia (also known as "chronic lymphoid leukemia" or "CLL"), is a type of leukemia, or cancer of the white blood cells (lymphocytes). CLL affects a particular lymphocyte, the B cell, which originates in the bone marrow, develops in the lymph nodes, and normally fights infection. In CLL, the DNA of a B cell is damaged, so that it can't fight infection, but it grows out of control and crowds out the healthy blood cells that can fight infection.

Acute lymphoblastic leukemia (ALL), is a form of leukemia, or cancer of the white blood cells characterized by excess lymphoblasts. Malignant, immature white blood cells continuously multiply and are overproduced in the bone marrow. ALL causes damage and death by crowding out normal cells in the bone marrow, and by spreading (metastasizing) to other organs. ALL is most common in childhood with a peak incidence at 4-5 years of age, and another peak in old age. The overall cure rate in children is 85%, and about 50% of adults have long-term disease-free survival. 'Acute' refers to the undifferentiated, immature state of the circulating lymphocytes ("blasts"), and to the rapid progression of disease, which can be fatal in weeks to months if left untreated.

Current treatment options of B-cell malignancies, including non-Hodgkin's lymphomas depend on the type and stage of malignancy. Typical treatment regimens include radiation therapy, also referred to as external beam therapy, chemotherapy, immunotherapy, and combinations of these approaches. One promising approach is radioimmunotherapy (RIT). With external beam therapy, a limited area of the body is irradiated. With chemotherapy, the treatment is systemic, and often adversely affects normal cells, causing severe toxic side-effects. Targeted RIT is an approach in which a B-cell specific antibody delivers a toxic substance to the site of tumor. The therapeutic potential of RIT in patients with B-cell NHL has been shown using different targets, including CD20, CD19, CD22, and HLA-DR10 (Lym-1). More recently, combined modality therapy (CMT) has become an increasingly frequent maneuver for the treatment of solid tumors, and includes radiosensitization of cancer cells by drugs, and the direct cytotoxic effect of chemotherapy. The most common chemotherapy regiment for treating NHL is Cyclophosphamide-Hydroxydoxorubicin-Oncovin (vincristine)-Prednisone (CHOP) combination therapy. A randomized study of aggressive, but early stage NHL showed superior results with CHOP plus involved field radiation over treatment with CHOP alone. Despite its promise, the disadvantage of treatments involving external beam radiation is that external beam radiation can only be delivered in high doses to a limited region of the body, while NHL is mostly widespread. Accordingly, CMT has proven clinically useful for locally advanced malignancies.

Another current approach is combined modality radioimmunotherapy (CMRIT), which pairs the specific delivery of systemic radiation (e.g., 90Y-DOTA-peptide-Lym-1) to NHL with the systemic radiation sensitizing effects of an additional chemotherapeutic agent. Because in CMRIT radiation is delivered continuously, cancer cells that are hypoxic may re-oxygenate, or pass through the radiosensitive G2/M phase of the cell cycle during the course of treatment, making cure more likely. In addition, CMRIT provides specificity first, by the specific targeting of NHL by Lym-1, and second by timing. This allows the radiation sensitizer to potentially synergize only at the sites targeted by RIT, thus maximizing efficacy and minimizing toxicity. Several previous xenograft studies have demonstrated improved synergy when the radiation synthesizer (Taxol) was given 24-48 hours after RIT.

Although CMRIT is currently viewed as the most advanced therapeutic approach for the treatment of NHL, the engineered conjugate (e.g., bispecific immunotoxin) of the present invention alone have been demonstrated to provide superior results in terms of tumor cell killing and overall survival, when tested in vitro and in the well accepted Raji and Daudi lymphoma xenograft models.

VII. Combination Treatments

In order to increase the effectiveness of a targeted delivery of therapeutic agents to targeted cells such as B cells in a subject, it may be desirable to combine these targeting conjugates or compositions with other agents effective in the treatment of a cancer or a B-cell malignancy, such as anti-cancer agents.

An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

In the context of the present invention, it is contemplated that the targeted therapy of the present invention could be used in conjunction with chemotherapeutic, radiotherapeutic, immunotherapeutic intervention, or other pro-apoptotic or cell cycle regulating agents.

Alternatively, the targeted therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, the targeted therapy of the present invention is "A" and the secondary agent, such as radio- or chemotherapy, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the therapeutic targeting conjugates of the present invention to a patient will follow general protocols for the administration of chemotherapeutics, taking into account the toxicity, if any, of the targeting conjugates. It is expected that the treatment cycles would be repeated as necessary. It also is contemplated that various standard therapies, as well as surgical intervention, may be applied in combination with the described targeted cell therapy.

A. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent to serve as a second targeting conjugate. Alternatively, the effector may be a lymphocyte carrying a surface molecule that interacts, either directly or indirectly, with a tumor cell target. Various effector cells include cytotoxic T cells and NK cells.

In certain aspects, the targeting conjugate may comprise an antibody or fragment thereof for immunotherapy. Alternatively, Immunotherapy could be used as part of a combined therapy, in conjunction with the targeted therapy. The general approach for combined therapy is discussed below. Generally, the tumor cell must bear some additional marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Gene Therapy

In yet another embodiment, the secondary treatment is a gene therapy in which a therapeutic polynucleotide is administered before, after, or at the same time the targeting conjugate is delivered. Delivery of a targeting conjugate in conjunction with a vector encoding one of the following gene products will have a combined anti-hyperproliferative effect on target tissues. A variety of proteins are encompassed within the invention, some of which are described below.

The tumor suppressor oncogenes function to inhibit excessive cellular proliferation. The inactivation of these genes destroys their inhibitory activity, resulting in unregulated proliferation. For example, the tumor suppressors p53, p16 and C-CAM may be used.

Another inhibitor of cellular proliferation is p16. The major transitions of the eukaryotic cell cycle are triggered by cyclin-dependent kinases, or CDK's. $p16^{INK4}$ belongs to a newly described class of CDK-inhibitory proteins that also includes $p16^B$, p19, $p21^{WAF1}$, and $p27^{KIP1}$. Restoration of wild-type $p16^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

Regulators of programmed cell death may also be used in the present invention for a combined therapy. Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1α, MIP-1β, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

VIII. Pharmaceutical Compositions

Where clinical applications are contemplated, it may be necessary to prepare pharmaceutical compositions—expression vectors, virus stocks, proteins, antibodies and drugs—in a form appropriate for the intended application. Generally, this will entail preparing disclosed targeting conjugate compositions that are essentially free of impurities that could be harmful to humans or animals.

One generally will desire to employ appropriate salts and buffers to render delivery vectors stable and allow for uptake by target cells. Buffers also are employed when recombinant cells are introduced into a patient. Aqueous compositions of the present invention may comprise an effective amount of a protein, peptide, fusion protein, recombinant phage and/or expression vector, dissolved or dispersed in a pharmaceutically acceptable carrier or aqueous medium. Such compositions also are referred to as innocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the proteins or peptides of the present invention, its use in therapeutic compositions is contemplated. Supplementary active ingredients also can be incorporated into the compositions.

The active compositions of the present invention may include classic pharmaceutical preparations. Administration of these compositions according to the present invention are via any common route so long as the target tissue is available via that route. This includes oral, nasal, buccal, rectal, vaginal or topical. Alternatively, administration may be by orthotopic, intradermal, subcutaneous, intramuscular, intraperitoneal, intraarterial or intravenous injection. Such compositions normally would be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it is preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

IX. Kits

In various aspects of the invention, a kit is envisioned containing therapeutic agents, diagnostic and/or delivery agents. In some embodiments, the present invention contemplates a kit for preparing and/or administering a therapy of the invention. The kit may comprise one or more sealed vials containing any of the pharmaceutical compositions of the present invention. In some embodiments, the lipid is in one vial, and the nucleic acid component is in a separate vial. The kit may include, for example, at least one conjugate comprising a targeting moiety with a VL-VH structure and a therapeutic agent, such as a toxin, one or more lipid component, as well as reagents to prepare, formulate, and/or administer the components of the invention or perform one or more steps of the inventive methods. In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill. The instruction information may be in a computer readable media containing machine-readable instructions that, when executed using a computer, cause the display of a real or virtual procedure of delivering a pharmaceutically effective amount of a therapeutic agent.

X. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of DT2219 Variants

For these studies, three different variations of DT2219 were synthesized, DT2219EA, DT2219EB1, and DT2219ARL.

Construction of DT2219EA.

In 2005, the inventors reported an original DT2219 2760 bp construct called DT2219EA constructed using DNA shuffling and assembly PCR (Vallera et al., 2005). DT2219 consisted of an NcoI restriction site at the N-terminus, followed by a downstream ATG initiation codon, the first 389 amino acids of the DT (DT390), the VH and VL regions of anti-CD22 (sFv) and anti-CD19 (Kipriyanov et al., 1996) linked by a 20 amino acid segment of human muscle aldolase (hma), and a Xho1 compatible restriction site (FIG. 1A). Importantly, Salvadore et al. (2002) reported that mutating three amino acids Thr-His-Trp (THW) in place of Ser-Ser-Tyr (SSY) at positions 100, 100A, and 100B in the CDR3 region of the VH of the anti-CD22 sFv enhanced its affinity, so these same amino acids were mutated in the assembled plasmid called pDT2219hmaEA.pET21d, which produced DT2219EA (enhanced affinity). The synthesis of the DT gene fragment was previously described (Chan et al., 1995) using diphtheria toxin CRM107 as a template. The hma fragment was used as a non-immunogenic linker to connect the two sFvs and was used to enhance the level of protein production and ultimately the level of purity of the molecule. HMA is 363 amino acids in length and the inventors used the final 20 amino acids (PSGQAGAAASESLFVSNHAY (SEQ ID NO:13)). DNA sequencing analysis (University of Minnesota, Advanced Genetic Analysis Center) was used to verify that the gene had been cloned in frame and was correct in sequence.

Construction of DT2219EB1.

DT2219EB1 was created by mutating DT2219EA by modifying two hot spot amino acids (S30G and N31R) in the anti-CD22 VL region as previously reported by Ho et al. (2005). The sequence change was verified.

Construction of DT2219ARL.

The hybrid gene encoding DT2219ARL was synthesized using assembly PCR. The major differences between DT2219ARL and DT2219EA were (1) reversal of the orientation of the VH and VL chains. In DT2219ARL, the VL preceded the VH (FIG. 1A). (2) The VL and VH genes of each sFv were conjoined by a fragment encoding the ARL linker (GSTSGSGKPGSGEGSTKG (SEQ ID NO:14)) and the two sFv genes were linked by a fragment encoding G4S linker. In its final configuration, the DT2219ARL Nco1/Xho1 gene fragment encoded a start codon followed first by 389 aa of DT, and then a 7 aa linker EASPEEA, followed by the anti-CD22 sFv, and then the CD19 sFv. The final target gene was spliced into pET21d vector expression vector and inclusion bodies expressed. A Food and Drug Administration (FDA) Investigational New Drug (IND) Application is now approved for the clinical phase I evaluation of DT2219ARL.

As specificity controls for these studies, the inventors constructed a bivalent fusion protein consisting of DT390 fused to two repeating sFvs recognizing human CD3epsilon called Bic3 (Vallera et al., 2005). Anti-CD3epsilon recognizes a domain of the T cell receptor (Vallera et al., 1996). An additional control included DT390EpCam23, DT390 spliced to anti-EpCam sFv and anti-ErbB2sFv sFv. Anti-EpCam and anti-ErbB2sFv have been used by others to synthesize recombinant IT (Di Paolo et al., 2003; Batra et al., 1991). ErbB2 is a tumor-associated antigen belonging to the epidermal growth factor receptor family and implicated in poor prognosis and more aggressive course in many human cancers including breast, lung, ovary and stomach (Menard et al., 2003).

Example 2

Expression and Purification of DT2219 Variants

To test activity of DT2219 variants, these recombinant immunotoxins were expressed and purified. Plasmid was transformed into the *Escherichia coli* strain BL21(DE3) (EMD, Madison Wis.). Bacteria were grown in 600 ml Luria Broth supplemented with 100 µg/ml carbenicillin in a 2 l flask at 37° C. with shaking. Expression of the hybrid gene was induced by the addition of isopropyl-b-D-thiogalactopyranoside (IPTG, FisherBiotech Fair Lawn, N.J.). Two hours after induction, the bacteria were harvested by centrifugation. The cell pellets were suspended and homogenized using a polytron homogenizer. After sonication and centrifugation, the pellets were extracted with 0.3% sodium deoxycholate, 5% Triton X-100, 10% Glycerin, 50 mM Tris, 50 mM NaCl, 5 mM EDTA, pH 8.0 and washed.

The proteins were refolded using a sodium N-lauroyl-sarcosine (SLS) air oxidation method modified from a previously reported procedure for isolating sFv (Vallera et al., 2005). Refolded DT2219 variants were purified by FPLC ion exchange chromatography (Q Sepharose Fast Flow, Sigma, St. Louis, Mo.) using a continuous gradient from 0.2 M to 0.5 M NaCl in 20 mM Tris-HCl, pH 9.0 over 4 column volumes.

Following ion exchange chromatography, 95 kDa DT2219ARL, DT2219EA, and DT2219EB1 were greater than 95% pure as determined by Coomassie blue staining (FIG. 1B).

Example 3

Cytotoxicity of Various Immunotoxins (IT) on the Daudi Cancer Cell Line

Figure 2B:
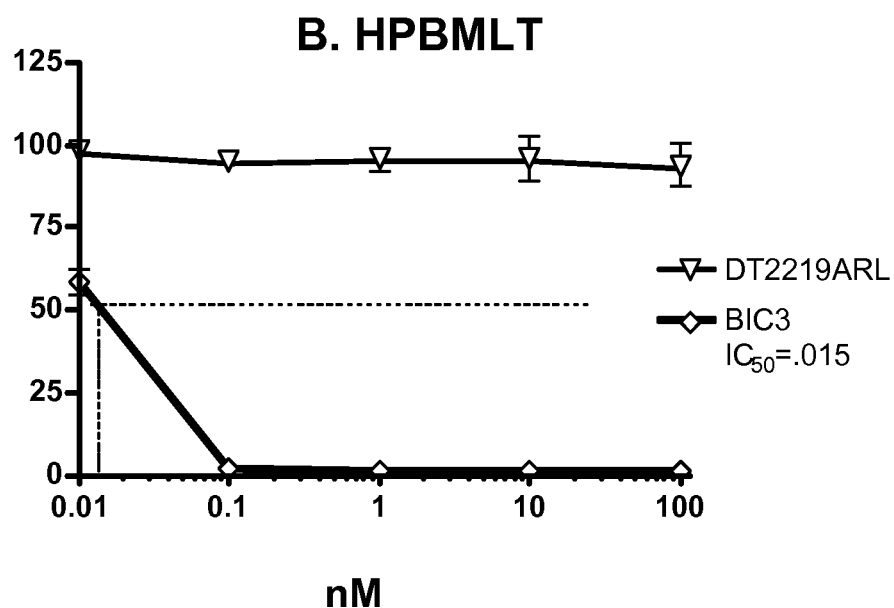
Figure 2C:
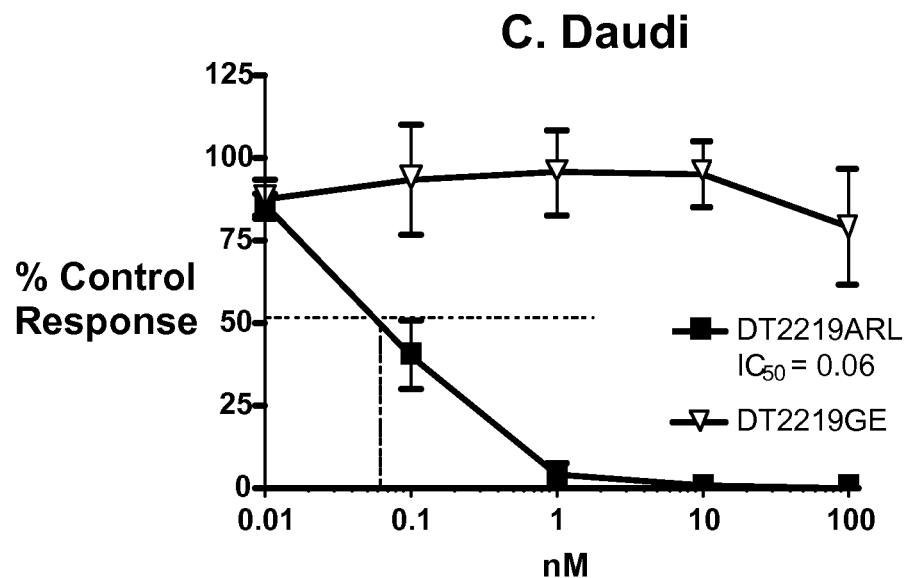

To test cytotoxicity of various immunotoxins (IT), Daudi was selected as a target cell line in these studies because flow cytometry studies showed greater than 95% positivity for both CD19 and CD22. To determine the ability of DT2219ARL, DT2219EA, or DT2219EB1 to kill Daudi, these IT were tested in a proliferation assay and a representative experiment is shown (FIG. 2A). DT2219ARL showed an $IC_{50}$ of 0.2 nM. DT2219EA showed an $IC_{50}$ of 0.4 nM. DT2219EB1 showed an $IC_{50}$ of 0.1 nM. None of these curves statistically differed. FIG. 2B shows a different experiment in which DT2219ARL had no effect on $CD22^-CD19^-$ HPBMLT T leukemia cells. In contrast, HPBMLT were readily killed with an anti-T cell IT called Bic3. To create the mutant DT2219GE gene, the DT2219 gene was disrupted by a single glycine to aspartic acid mutation at position 53 of the DT390 molecule known to inactivate the catalytic activity of the DT A chain. Whereas parental DT2219ARL showed an $IC_{50}$ of 0.06 nM, the mutated DT2219GE protein minimally inhibited Daudi proliferation. Together, these data showed that DT2219 variants were potent and selective in their ability to inhibit $CD22^+CD19^+$ target cells and that the killing of DT2219 IT is caused by the DT moiety, not the 2219 moiety (FIG. 2C). Trypan blue viability assays were performed in addition to proliferation assays and as an additional check to verify that DT2219ARL was indeed killing and not simply inhibiting cell proliferation/protein synthesis.

Figure 2D:
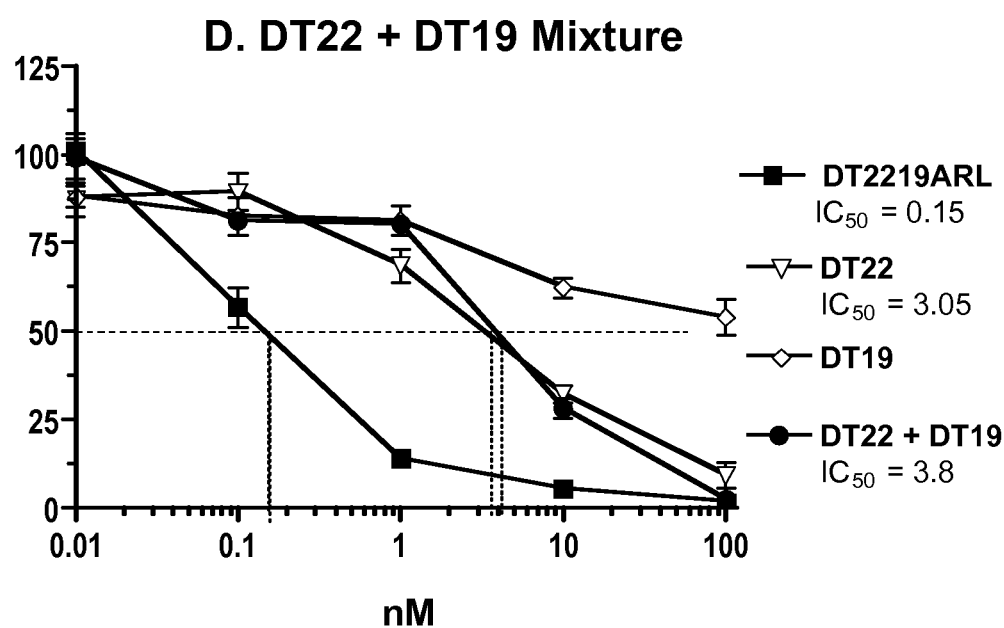

Furthermore, increased activity of DT2219ARL is due to the presence of the anti-CD22 and anti-CD19 sFv ligands on a single molecule. Proliferation assays were conducted in order to determine if the increased activity of DT2219ARL was a result of the increased number of binding molecules present on a bispecific IT. FIG. 2D shows the data comparing the activity DT2219ARL to the monospecific DT22 and DT19, as well as a combination of both monospecific IT against Daudi cells. A mixture of DT22 and DT19 resulted in an identical number of ligands as are present in the same concentration of DT2219ARL. Against Daudi, the monospecific DT22 was able to kill with an $IC_{50}$ of 3.05 nM. Monospecific DT19 was less effective. However, DT2219ARL showed an $IC_{50}$ of 0.15 nM, representing about a 1000-fold increase in activity as compared to DT19 and a 20-fold increase in activity as compared to DT22. Interestingly, a mixture of DT22 and DTIL19 showed no increase in activity over DT22 alone. These data demonstrate the superior activity of DT2219ARL is due to the presence of both ligands on a single-chain molecule.

Antibodies and Cell Lines.

The anti-CD19 monoclonal antibody hybridoma HD37 that secretes mouse IgG1 kappa has been previously described by Dorken et al. (1983) and has been studied as a targeted toxin conjugated to ricin toxin A chain (Stone et al., 1996). RFB4 (anti-CD22) was provided by Dr. Ellen Vitetta, University of Texas Southwestern Medical Center, Dallas, Tex. Anti-Ly5.2, a rat IgG2a from clone A20-1.7, generously provided by Dr. Uli Hammerling, Sloan Kettering Cancer Research Center, New York, N.Y. Anti-Ly5.2 was used as a control since it recognized mouse CD45.1, a hematopoietic cell surface marker not expressed on human cells.

Human cell lines included the CD19⁻CD22⁻ T cell leukemia HPBMLT Morikawa et al., 1978) and the CD22⁺19⁺ Burkitt's lymphomas Daudi (Klein et al., 1968) and Raji Pulbertafi, 1964). Raji was genetically altered by transfection with dual reporter genes encoding both firefly luciferase and GFP creating the Raji-luc cell line for imaging. Raji-luc was subcloned using flow cytometric cell sorting in order to obtain stable transfectants that were highly bioluminescent.

Measuring DT2219ARL Activity In Vitro.

To determine the effect of DT2219 on normal B and malignant B cell function, the Daudi CD19⁺CD22⁺ Burkitt's lymphoma cell line was used. Flow cytometry shows that Daudi is >98% positive for both CD19 expression and CD22 expression. Cells ($10^5$) were plated in a 96-well flat-bottom plate in RPMI supplemented with 10% fetal bovine serum, 2 mM L-glutamine, 100 U/ml penicillin, 100 µg/ml streptomycin. Immunotoxin in varying concentrations was added to triplicate wells containing cells. The plates were incubated at 37° C., 5% $CO_2$ for 72 h. Cells were then incubated with 1 µCi [methyl-$^3$H]-thymidine (GE Healthcare, UK) per well for 8 h and harvested onto glass fiber filters, washed, dried and counted for 10 min in a standard scintillation counter. Data were analyzed using Prism 4 (GraphPad Software, Inc.) and were presented as "percent control response" calculated by dividing the cpm of untreated cells by the cpm of the immunotoxin-treated cells (×100).

Statistical Analyses.

Groupwise comparisons of continuous data were made by Student's t-test. A computer program for compiling life table and statistical analysis by the Log-Rank test was used to analyze survival data. Probability (p) values <0.05 were considered significant

Example 4

Blocking DT2219 Activity

Figure 3A:
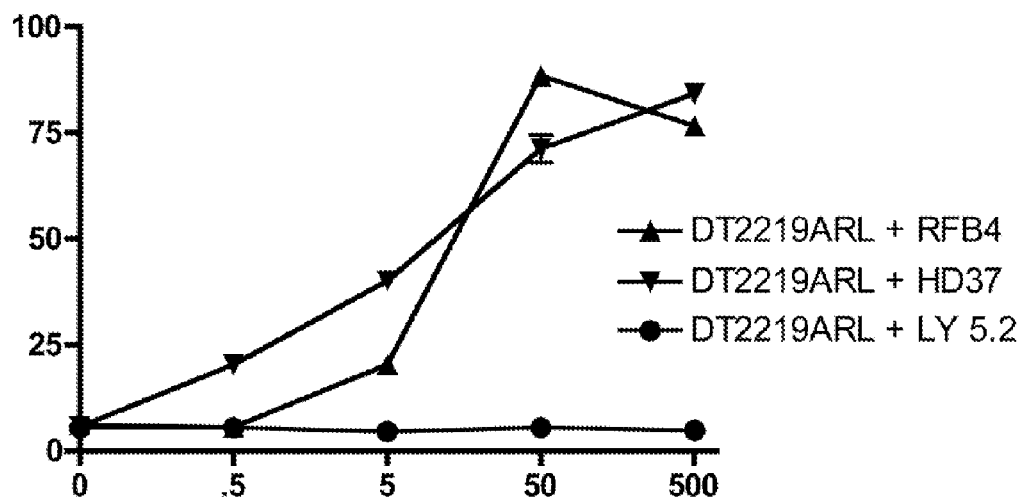
FIGS. 3A-C. The activity of mutated DT2219ARL is mediated by both anti-CD19 sFv and the anti-CD22 sFv ligands. Proliferation studies were performed in which Daudi cells were treated with a constant concentration of 10 nM DT2219ARL (FIG. 3A), DT2219EA (FIG. 3B), or DT2219EB1 (FIG. 3C) and then blocked with increasing concentrations of HD37 monoclonal antibody, RFB4 monoclonal antibody, or non-reactive control Ly5.2 antibody. Thymidine uptake was then measured. Each line represents the mean of triplicate determinations±standard deviation (SD). Percent blocking was calculated in comparison to the unblocked control and then graphed. Counts for untreated Daudi cells were 59,301±2,804 cpm/20,000 cells.
Figure 3B:
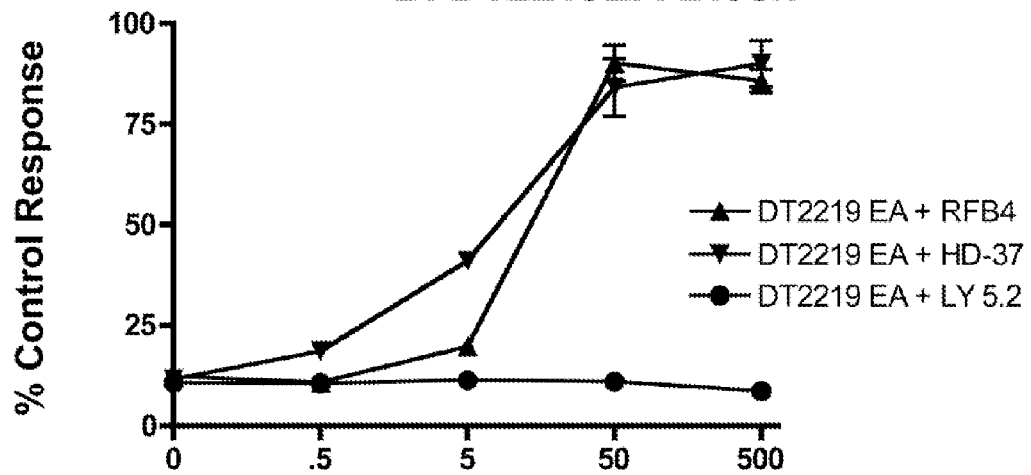
Figure 3C:
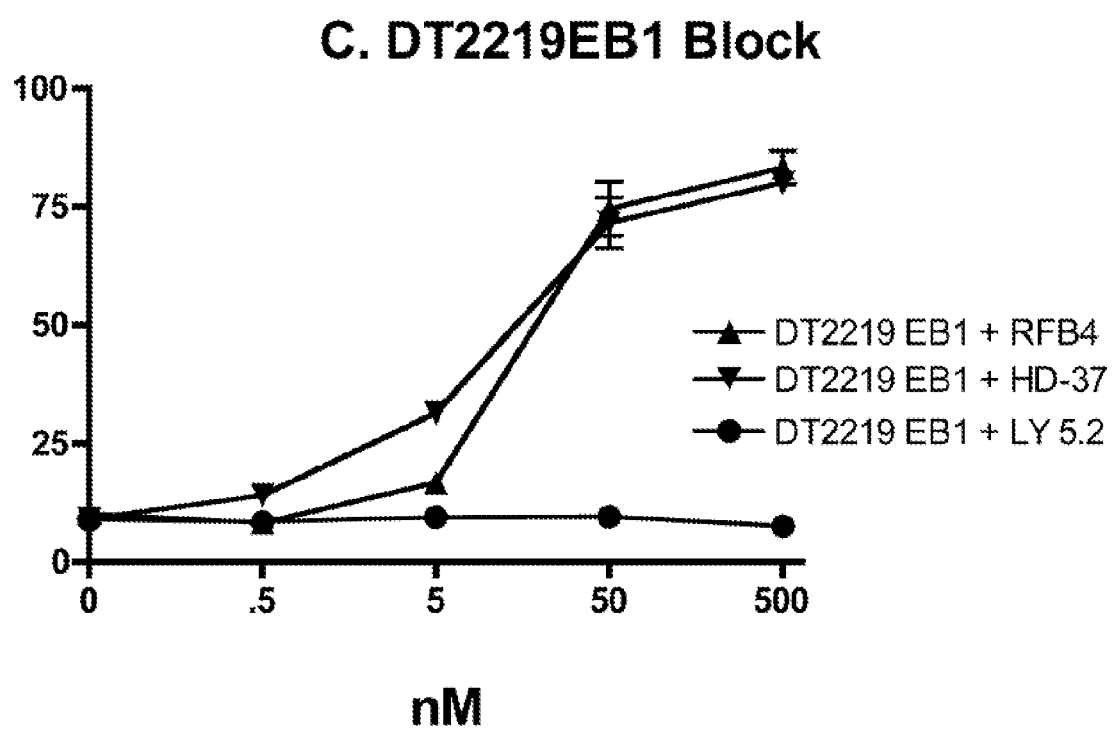

To confirm that the anti-CD19 sFv and anti-CD22 sFv ligands were both still active in DT2219, blocking experiments were performed with the parental RFB4 and HD37 monoclonal antibodies. Proliferation experiments were performed in which increasing amounts of blocking antibody were added to a constant inhibitory concentration of 10 nM DT2219 immunotoxin which inhibited about 90% of Daudi cell proliferation ($IC_{90}$). FIG. 3A shows that increasing concentrations of RFB4 or HD37 inhibit the proliferation of 0 nM DT2219ARL in a dose-dependent manner. Saturation is reached around 50 nM. The addition of an irrelevant control antibody anti-Ly5.2 had no effect. Neither antibody blocked 100% of the activity because blocking one ligand would not necessarily fully block the other. Similar results were observed when DT2219EA or DT2219EB1 were blocked in an identical fashion (FIGS. 3B-C). None of the antibodies alone were stimulatory to Daudi cells at these concentrations. Together, the similarity of these curves indicated that that the anti-CD19 and anti-CD22 ligands on the DT2219 variants appeared to bind with similar monovalent affinity. Also, both sFvs were active on the DT2219 molecules which were highly specific.

Blocking studies were conducted to test the specificity of DT2219ARL. Briefly, 0.5, 5, 50, or 500 nM RFB4 or HD37 were added to media containing 10 nM DT2219EA, DT2219EB1, or DT2219ARL. Resulting mixtures were added to wells containing Daudi cells and proliferation was measured by $^3$H-thymidine uptake as described. The mouse specific antibody Ly 5.2 was studied as a negative control. Data were presented as "percent control response" as described above.

Example 5

Target Cell Binding Flow Cytometry Studies

To determine whether the cytotoxicity data related to the ability of the various immunotoxins to bind their target, the recombinant immunotoxins were labeled with FITC and tested for target cell binding with flow cytometry. Briefly, Table 2 shows that DT2219ARL-FITC was highly reactive with normal human B cells in the form of PBMC with a $K_d$ of 28 nM. For these studies, the inventors gated the 7% B cells found in normal human peripheral blood. These findings were confirmed by testing DT2219ARL against magnetic bead enriched CD22⁺CD19⁺ B cells (enriched to 90%). The $K_d$ of the enriched cells was similar at 20 nM. When DT2219ARL was tested against human malignant B cell lines in the form of the Daudi and Raji cell lines, the $K_d$ of Daudi was 133 nM and Raji was 39 nM. These findings indicate that different $K_d$s can be anticipated on different cell lines, some lower than others.

Finally, the inventors tested DT2219ARL binding against human malignant B cells in the form of peripheral blood B-CLL from two different patients. Patient 1 had a $K_d$ of 36, while patient 2 had a $K_d$ of 181. Together, these data indicate that DT2219ARL will bind malignant B cells from patients, but patient-to-patient variation may be anticipated, perhaps due to variances in CD22 and CD19 expression levels. As a negative control the inventors tested the binding of irrelevant immunotoxins that do not bind to human B cells, DTEp-Cam23-FITC and Bic3-FITC. They showed a $K_d$ of 1879 and 1032 nM, respectively indicating that the binding of DT2219ARL is specific. These data suggest that there is no major difference in the binding of DT2219ARL to normal and malignant B cells and that binding is specific.

DT2219ARL was labeled with FITC using the standard labeling procedure and verified at 2-3 FITC molecules/DT2219ARL molecule. Cells were incubated with DT2219ARL-FITC in the dark, washed, and then run assayed on a Becton-Dickinson FACSCaliber. $K_d$ values were determined using PRISM software. R2 values indicate how well the regression plots fit data points.

TABLE 2

$K_d$ Values of DT2219ARL-FITC on various cells on malignant and normal B cells.

| | Kd (nM) | $R^2$ |
|---|---|---|
| Normal B Cells | | |
| Human PBMC | 28 | 0.90 |
| Enriched CD22⁺ Cells | 20 | 0.95 |
| Malignant B Cells (Cell lines) | | |
| Daudi | 133 | 0.97 |
| Raji | 39 | 0.99 |
| Malignant B Cells (Patient B-CLL cells) | | |
| Patient 1 | 36 | 0.97 |
| Patient 2 | 181 | 0.99 |
| Negative Control IT Binding to Raji | | |
| DTe23EpCAM-FITC | 1879 | 0.99 |

Figure 4:
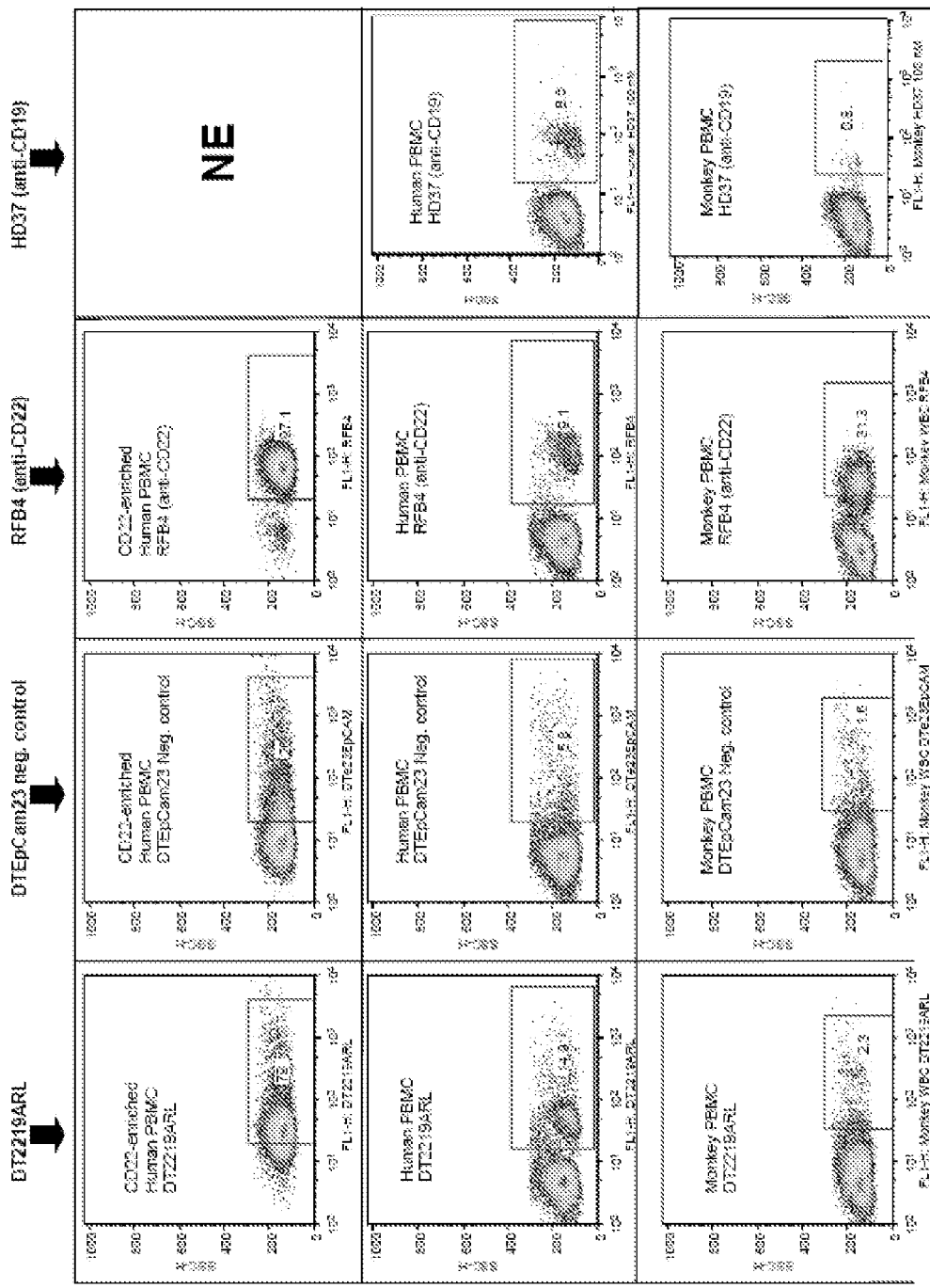
FIG. 4. Binding of DT2219ARL-FITC to monkey PBMC by direct immunofluorescence. Monkey PBMC, normal human PBMC, or normal human CD22⁺ magnetic bead enriched PBMC cells were incubated with DT2219ARL-FITC, or negative control DTEpCam23. Positive controls included FITC labeled conventional monoclonal antibodies RFB4-FITC or HD37-FITC. Flow cytometry was performed and data expressed as a contour plot showing cells versus increasing fluorescent intensity. The top 3 panels show human CD22⁺ magnetic bead enriched PBMC, the lowest 3 panels show normal monkey PBMC, while the middle 3 panels show normal human PBMC. The box in each panel outlines the gated area which shows binding that exceeds the values obtained for the negative control. The number in the box is the percentage of positive cells. NE—not evaluated.

To study the specific binding of DT2219ARL to cells, the reactivity of DT2219ARL-FITC with human PBMC, monkey PBMC, and magnetic bead enriched CD22+ human PBMC was compared (FIG. 4). The top 3 panels show that CD22 enriched human PBMC were highly reactive (79.1%) with a saturating concentration of DT2219ARL-FITC (100 nM). A negative control DTEpCam23-FITC was not as reactive with human CD22+ enriched PBMC. A control conventional anti-CD22-FITC antibody (RFB4) was highly reactive. In the same experiment, the lowest 3 panels show that DT2219ARL-FITC did not recognize monkey PBMC (2.28%), even though the positive control anti-CD22 antibody did recognize them (31.3%). The parental anti-CD19 antibody HD37 did not recognize monkey cells. The middle 3 panels showed that DT2219ARL-FITC did recognize human PBMC. The parental anti-CD22 and anti-CD19 monoclonal antibodies also recognized B cells in the peripheral blood. Note that there are considerably less positive B cells because these are PBMC and not a CD22-enriched population.

Flow cytometry studies. To determine comparative $K_d$s, DT2219ARL-FITC and control Bic3 (DT390 fused to two anti-CD3 sFv)-FITC and DTe23EpCAM-FITC were reacted with Daudi cells, Raji cells, normal human peripheral blood mononuclear cells (PBMC), normal human CD22+, magnetic bead enriched PBMC, and patient CLL cells. Cells were incubated with recombinant FITC-labeled proteins at saturating concentrations for 45 minutes at 4° C. Positive cells were quantitated using a Becton Dickinson FACS Calibur. Kds were calculated using PRISM software. DT2219ARL-FITC reactivity was also determined with non-human primate cells. Rhesus monkey PBMC cells were obtained through RAR, University of Minnesota. As controls, binding was simultaneously assessed against human PBMC and human CD22+, magnetic bead enriched PBMC enriched using a CD22 isolation kit and a MACS system (Miltenyi Biotec, Auburn, Calif.).

Example 6

Effects of DT2219 IT in SCID Mice with Systemic Cancer

Injection of the Daudi cells intravenously into SCID mice results in a systemic tumor that infiltrates all major organs and is reminiscent of human leukemia. To determine if DT2219ARL was effective against established systemic leukemia and whether it differed in its effectiveness from DT2219EB1, systemic cancer was initiated in mice and ip treatments were started on day 3. FIG. 5A shows that mice given 6 ip injections of DT2219ARL survived significantly longer than mice given treatment with DT2219EB1 or untreated mice (p<0.001). All of the DT2219ARL treated mice survived to day 90 when the experiments were terminated. All of the untreated control mice and the DT2219EB1 treated mice were dead by day 90. Three of five mice given DT2219EB1 died early by day 10 with weight loss indicating that DT2219EB1 is more toxic than DT2219ARL. FIG. 5B shows a different experiment in which mice were given 11 injections of DT2219ARL. Again, all of these mice survived 150 days compared to groups of mice treated with control Bic3 or untreated controls (p<0.001). DT2219EA also showed enhanced survival, but over 60% of these mice were dead by day 80. No early toxic deaths resulted from DT2219EA or DT2219ARL treatment. FIG. 5C shows that when mice are given a single dose of DT2219ARL survival is significantly better than untreated controls (p<0.01). DT2219EA also shows a protective effect that is not as pronounced as the effect with DT2219ARL.

Figure 6A:
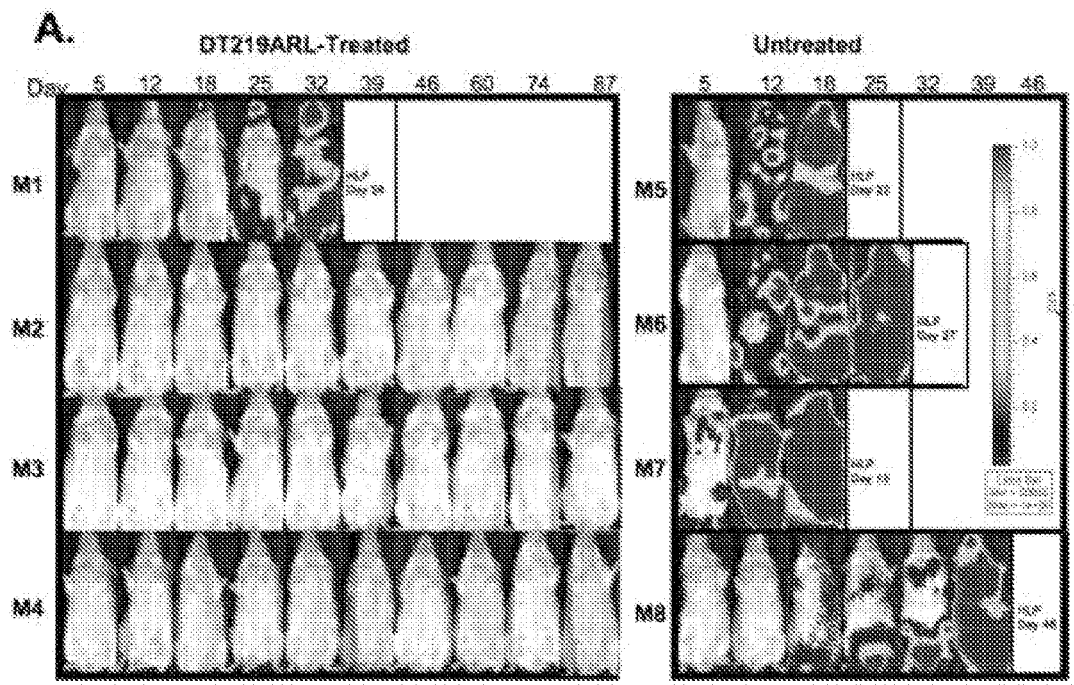
FIGS. 6A-C. Effect of ip administration of DT2219ARL on mice given systemic B cell cancer by IV injection of Raji-luc. Raji-luc cells stably expressing the luciferase gene were administered IV to SCID mice.
Figure 6B:
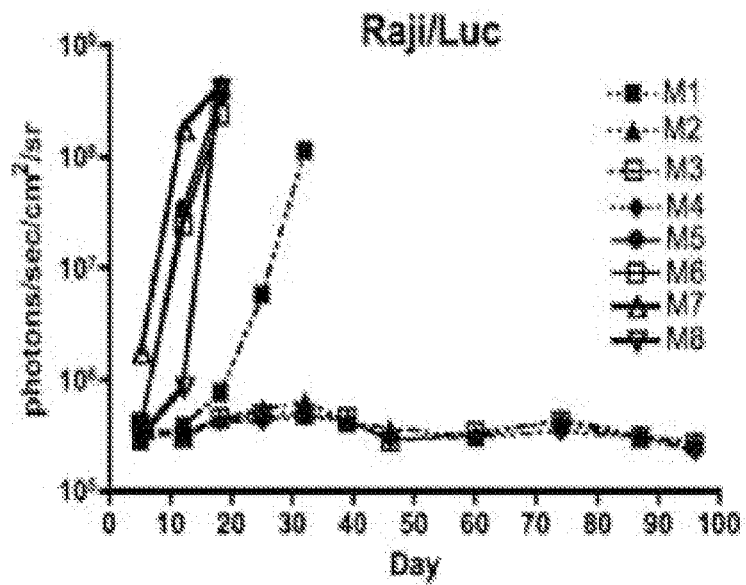
Figure 6C:
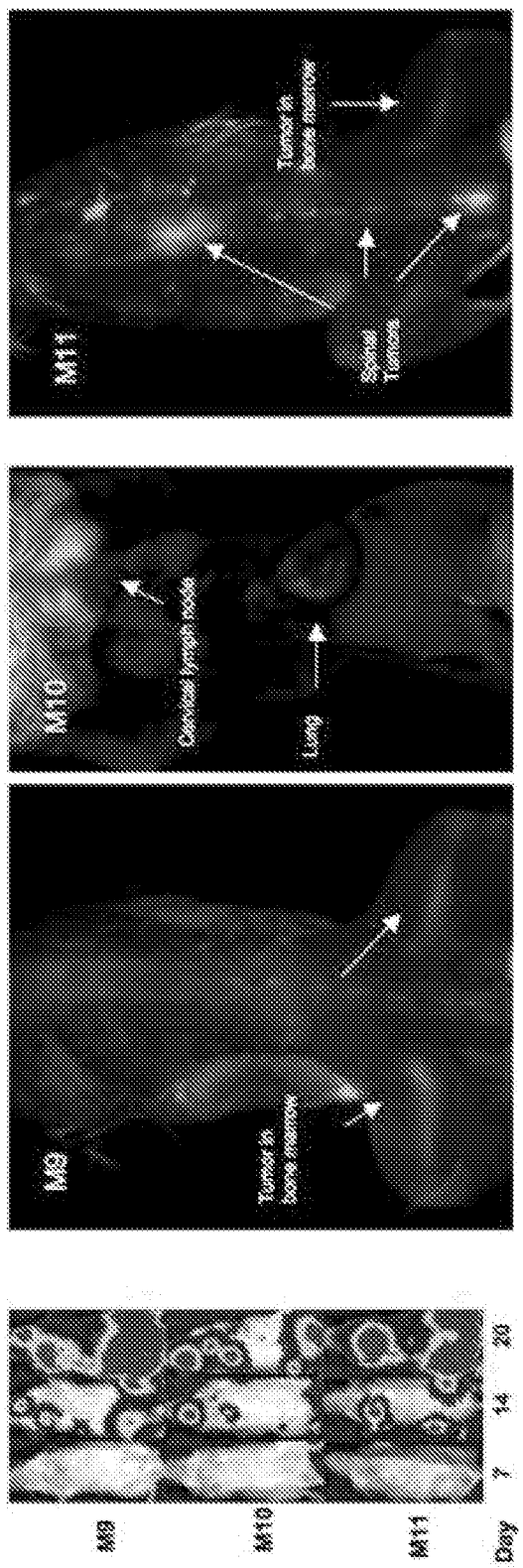

To study a second human B cell malignancy in a model which could be imaged in real time, Raji-luc was injected intravenously into SCIDs to induce systemic cancer. FIG. 6A shows that tumor progressed quickly since it was detected in all untreated mice (n=4/group) by day 12-18 and all untreated mice developed hind limb paralysis on days 18 through 46. Animals injected with Raji-luc develop this CNS complication with a 100% incidence. Three of four (75%) of the DT2219ARL treated mice were completely tumor-free on day 87. Tumor progressed in one of the treated mice on day 18. FIG. 6B shows the total photon activity graphed over time for each mouse. In FIG. 6C, three additional mice were injected with Raji-luc and not treated in order to study the aggressive nature of the tumor with a dual reporter gene cell line. Luciferase bioluminescent imaging showed these animals all developed tumor by day 14. GFP imaging of the same mice on day 21 confirmed tumor presence in lung and immune system and revealed the tumor had a propensity for the bone marrow and spinal cord.

Together, these data indicate that DT2219ARL was able to prevent the onset of established fatal systemic cancer in two highly aggressive human B cell malignancy models in SCID mice.

Mouse Efficacy Studies.

Female SCID/hu mice were purchased from NCI, Frederick Cancer Research and Development Center, Animal Production Area and housed in an AAALAC-accredited specific pathogen-free facility under the care of the Department of Research Animal Resources, University of Minnesota. Animal research protocols were approved by the University of Minnesota Institutional Animal Care and Use Committee (IACUC). Animals were housed in microisolator cages to minimize the possibility of transmission of any contaminating virus.

In Experiment 1 (FIG. 5A), $10^6$ Daudi cells in 200 μl sterile, endotoxin-free PBS were injected intravenously into SCID mice via caudal vein. After Daudi injection on day 0, one 20 μg IV injection of DT2219ARL or DT2219EB1 was given on day 3 with five subsequent 10 μg/200 μl ip injections on days 5, 10, 24, 26 and 31. Body weights were documented three times per week. Since this Daudi substrain always metastasizes to the central nervous system resulting in hind-limb paralysis (HLP), paralyzed mice were deemed pre-terminal and euthanized by University approved IACUC procedures.

In Experiment 2 (FIG. 5B), mice were given $10^6$ Daudi cells IV on day 0 and divided into groups. Groups of 7 mice (no treatment group, n=5) were given ip injections of 20 μg/200 μl DT2219ARL, DT2219EA, or Bic3 on days 3 and 6; 10 μg/200 μl ip injections on days 21, 24, 26, 31, 38, 47, 54, 56 and 59.

In Experiment 3 (FIG. 5C), mice were given $10^6$ Daudi cells IV on day 0. A single 20 μg ip injection of DT2219ARL or DT2219EA was given on day 3. Body weights were determined. Mice exhibiting hind limb paralysis were euthanized.

In Experiment 4 (FIG. 6), to test the efficacy of DT2219ARL against a different CD22+CD19+ human B cell malignancy, mice were given $10^6$ Raji-luc cells IV on day 0 and then were treated with a single 20 μg ip injection of drug on days 3, 5, 11, 16, and 18. Mice were imaged on day 5, 12, 18, 25, 32, 39, 46, 60, 74, and 87. Images were captured using Xenogen Ivis imaging system (Xenogen Corporation, Hopkington Mass.) and analyzed with IGOR Pro 4.09a software (WaveMetrics, Inc., Portaland, Oreg.). Prior to imaging, mice were anesthetized using isoflorane gas. All mice received 100

µl of a 30 mg/ml D-luciferin aqueous solution (Gold Biotechnology, St. Louis, Mo.) as a substrate for luciferase 10 minutes before imaging. All images represent a 5 minute exposure time and all regions of interest (ROI) are expressed in units of photons/sec/cm$^2$/sr.

Example 7

Effects of DT2219ARL in Rabbits

Figure 7A:
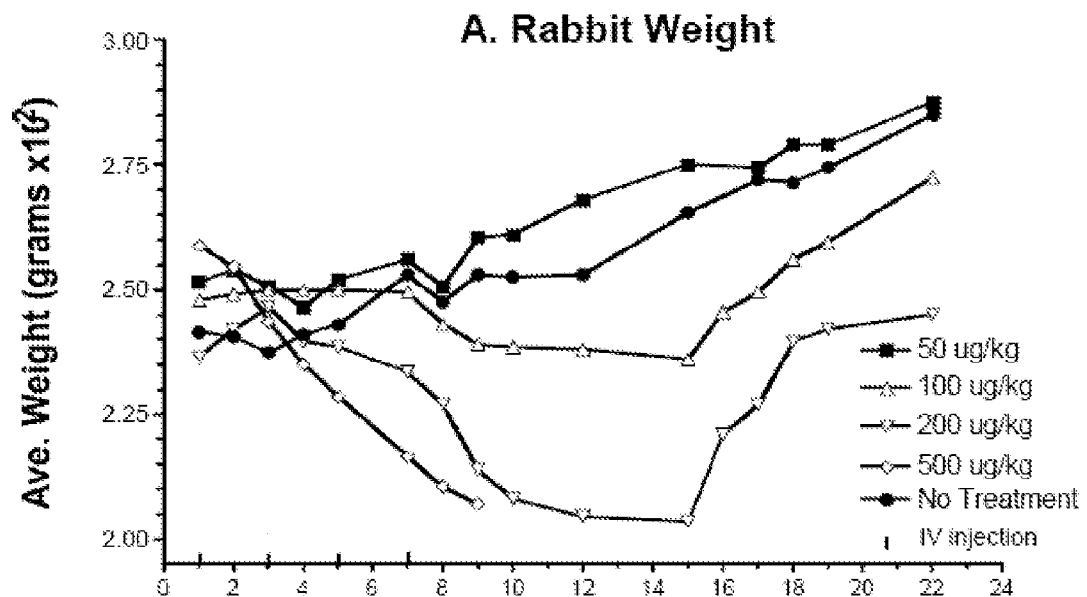
FIGS. 7A-C. Toxicity of DT2219ARL in rabbits. Rabbits were given IV injection of DT2219ARL on days 1, 3, 5, 7.

To determine the maximum tolerated dose (MTD) of DT2219ARL, rabbits were injected with a course of 4 IV injections given every other day. Rabbits were given either 50, 100, 200, or 500 µg/kg. Two animals were treated at each dosage. FIG. 7A shows the average weight loss and reveals a minimal effect at 50 or 100 µg/kg treatment as compared to the untreated controls. At 200 µg/kg there was a more pronounced weight loss amounting to less than 20% of starting weight that is not considered life threatening by the IACUC. Weight loss is likely due to non-specific toxicities of the agent, becoming obvious at higher doses. These are likely due to non-specific uptake of DT390, primarily causing liver damage.

Figure 7B:
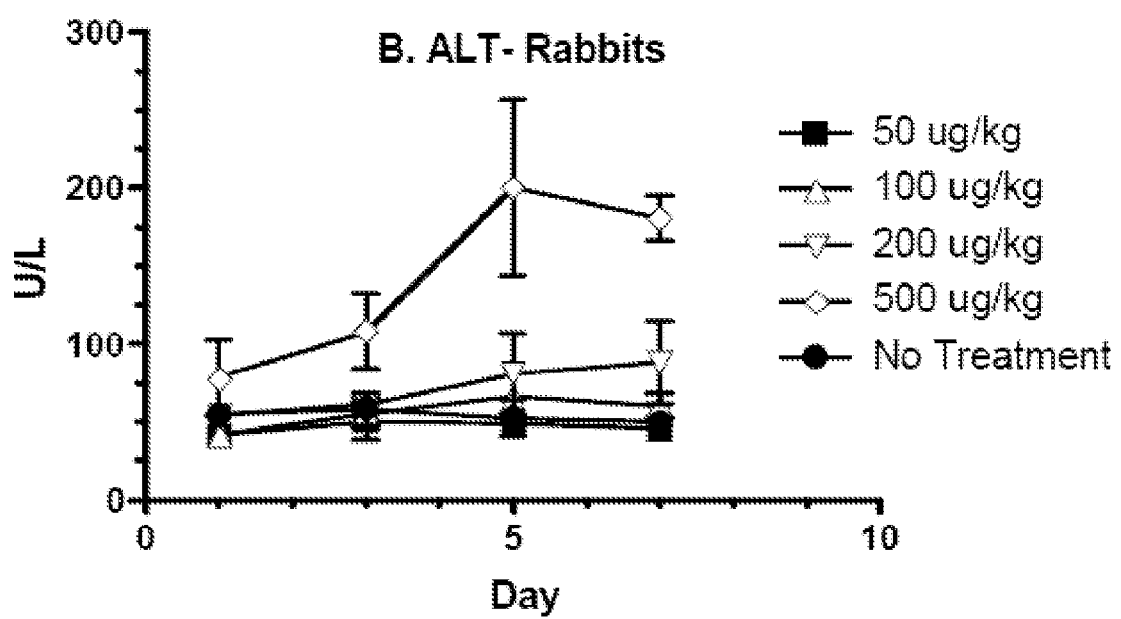
Figure 7C:
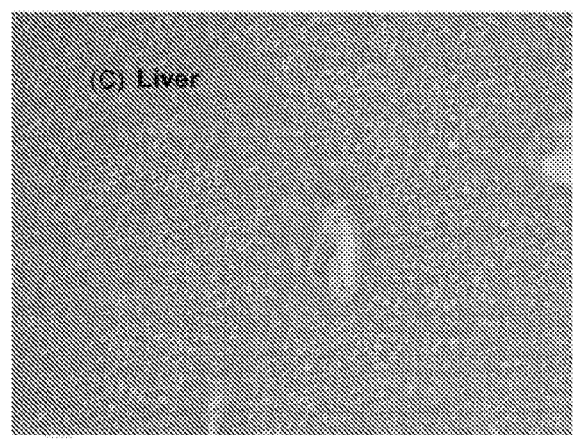

BUN (Blood-Urea-Nitrogen) levels correlated with increasing concentrations of DT2219ARL with only the 500 µg/kg dosage causing elevations. This increase only reached 100 mg/dL and was considered minimal and histology confirmed mild effects in the kidneys. In contrast, DT2219ARL was highly damaging to liver at 500 µg/kg, but not at 200 µg/kg. Not only did these animals lose weight, but FIG. 7B shows a precipitous rise in ALT levels indicating dose-dependent hepatic damage. Damage was confirmed by histology studies which showed necrosis and fatty degeneration consistent with grade 4 liver damage (FIG. 7C). Together, the ALT, histology, and weight data confirmed that the dose-dependent toxicity of DT2219ARL was likely due to non-specific uptake of DT390, primarily causing liver damage. The 50,000 µg/kg dosage damaged the liver and the MTD was 200 µg/kg. Histology studies of the heart, lung, and spleen did not show any evidence of cellular damage or toxicity.

In the rabbit studies, female New Zealand White rabbits (2.2 kg) were purchased from Bakkom Rabbitry (Viroqua, Wis.) and housed under the care of Resource Animal Resources as described above. Catheters were implanted in the ears for IV drug administration. Animals were weighed to determine the effect of drug on weight. Blood samples were obtained centrifuged immediately at 5000 rpm. Individual serum samples were analyzed on a Kodak ETA-CHEM 950 by the Clinical Chemistry Laboratory, University of Minnesota Hospital, Fairview (Minneapolis, Minn.). The BUN assays were read spectrophotometrically at 670 nm. In the ALT assay, the oxidation of NADH was used to measure ALT activity at 340 nm.

Example 8

Design and Cytotoxity of 2219 KDEL and 2219 KDEL 7 Mutants

This design of bispecific ligand-directed toxin (BLT) also works when the inventors used truncated *pseudomonas* exotoxin fused to 2219 scFvs instead of DT390. The PE has been genetically engineered to reduce its immunogenicity as reported by the Ira Pastan Lab (Alderson et al., 2009).

Figure 8:
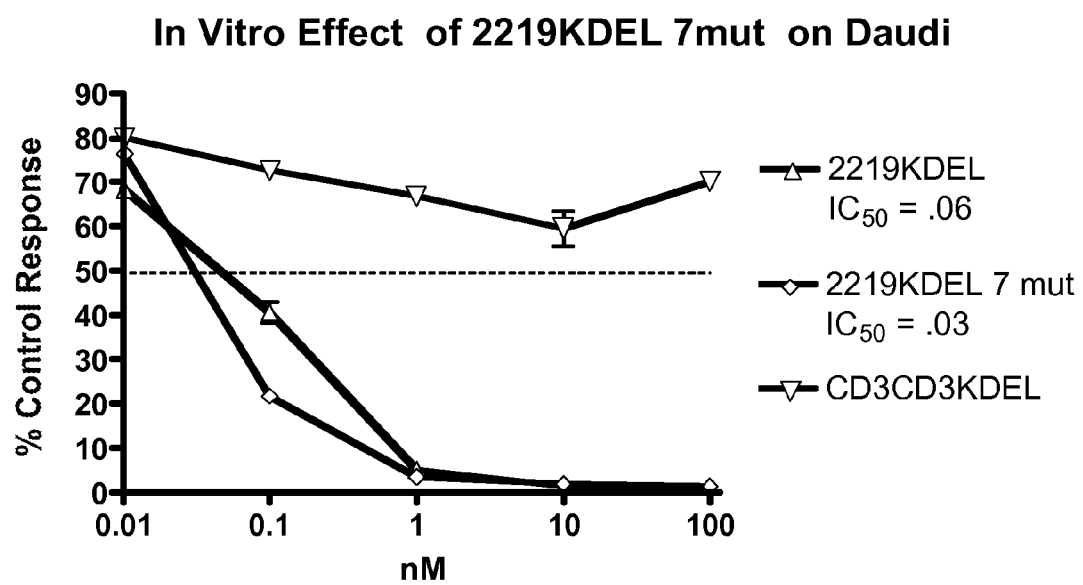
FIG. 8. In vitro Effect of 2219 KDEL 7mut on Daudi. Daudi cells were cultured with fusion proteins and proliferation was measured by uptake of tritiated thymidine. Data are percentage of control response where control response is untreated cells. Data are expressed as mean±standard deviation (SD). There is no difference in the activity of 2219 KDEL and 2219 KDEL7mut. CD3CD3 KDEL is an anti-T cell selectivity control immunotoxin not reactive with Daudi cells.
Figure 9:
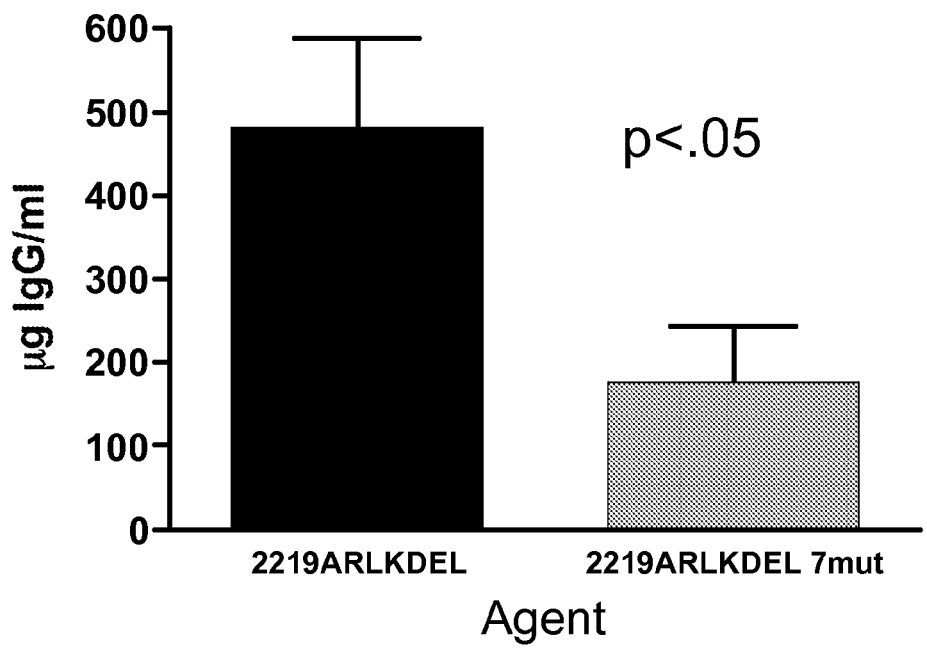
FIG. 9. Antibody Response to Immunization with 2219 KDEL or 2219 KDEL 7 mut. 2219 KDEL 7mut has reduced immunogenicity. To detect anti-toxin antibodies, immunocompetent BALB/c mice were immunized with either non-mutated parental 2219 KDEL or mutated 2219 KDEL. Serums from individual mice (n=5/group) were analyzed in a modified ELISA measuring ug/ml anti-toxin IgG. Data were represented as the average μg IgG/ml. The two groups significantly differed (p<0.05) and 2219 KDEL 7mut was not as immunogenic.
Figure 10:
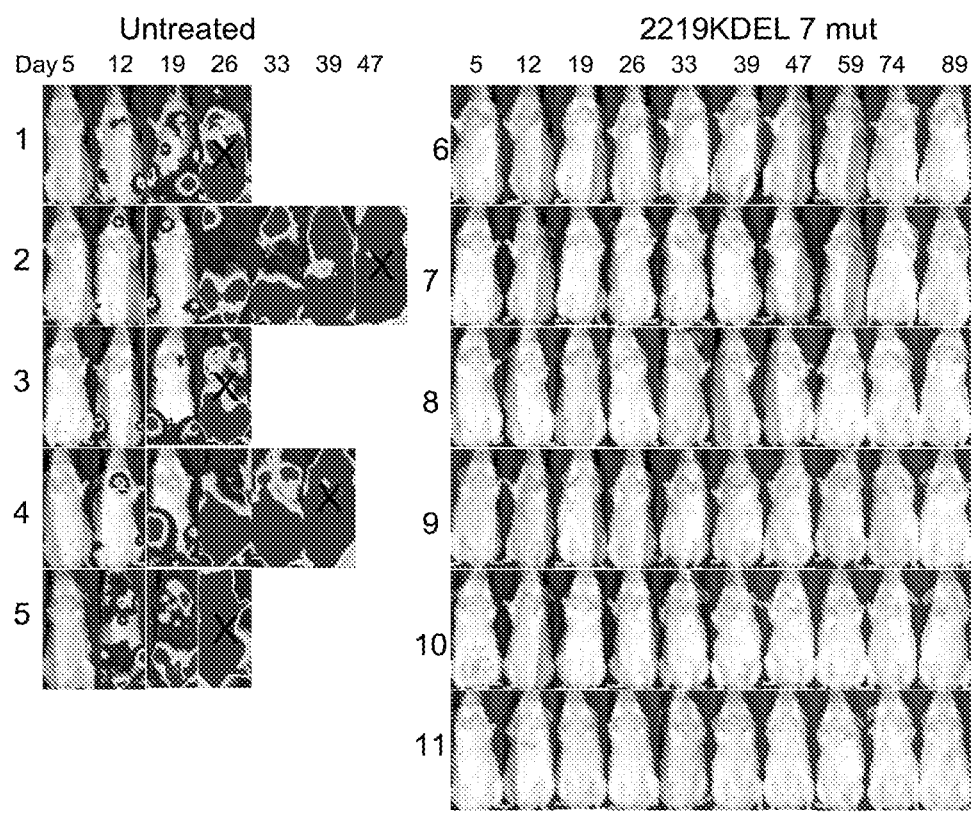
FIG. 10. Effect of ip administration of 2219 KDEL 7mut on mice given systemic B cell cancer by IV injection of $10^6$ Raji-luc. Raji-luc cells stably expressing the luciferase gene were administered IV to SCID mice. Mice were either treated ip with 2219 KDEL 7mut or untreated. Treatment schedule was injection/every other day (three times/week, MWF). This was called one "course of treatment." The mice were treated with 4 courses of 20 μg which began on days 3, 17, 31, 45. Luciferase bioluminescence was measured as photons/sec/$cm^2$/sr. Treatment resulted in cancer inhibition.

In order to determine if other toxins could be used, the inventors bioengineered a nucleotide sequence to express 2219 KDEL (protein sequence is SEQ ID NO:5; encoded by SEQ ID NO:6). In this instance, they fused the same 2219 scFvs from DT2219 to truncated PE. The amino acids KDEL were added to replace REDLK at the C-terminus of PE since this has been previously shown to enhance ER retention and enhance toxicity. Another mutant was created called 2219 KDEL 7mut (protein sequence is SEQ ID NO:7; encoded by SEQ ID NO:8) in which 8 hydrophilic amino acids on PE were mutated to reduce its immunogenicity (Onda et al., 2008; Pastan et al., 2009). Both 2219 KDEL and 2219 KDEL 7 mut were tested for their ability to inhibit Daudi cell proliferation in vitro (FIG. 8) and showed high cytotoxicity on Daudi cells.

Example 9

Clinical Trial of Phase I Study of DT2219ARL

Phase I clinical study was designed to determine the MTD (maximum tolerated dose) of DT2219ARL for treatment of chemotherapy refractory or relapsed and bone marrow transplant ineligible or bone marrow transplant relapsed B-cell lineage leukemia or relapsed B-cell lineage lymphoma. It is anticipated that approximately 36 patients will be needed for this phase I evaluation and that this study should be completed within 3 years.

Immunophenotypic analysis of lymphoblasts from children and adults with B-lineage ALL demonstrate that virtually all (>95%) have expression of CD19 and >80% express CD22 (Frankel et al., 2002; Bene, 2005). The marked prevalence of both markers on the tumor cells should allow for effective targeting of DT2219ARL.

DT2219ARL protein is supplied frozen in sterile 1 mL colorless, type I glass vials with an 11 mm rubber stopper and an aluminum seal ring and is formulated at 1 mg drug in 1 mL of 0.15 M NaCl/10 mM sodium phosphate+0.5% Polysorbate 80, pH 7.4. Lot #120706 will be used for this trial. Vials used in drug preparation were sterile pyrogen-free, 1 mL (Hollister Stier, Miles Inc. #280090-M01).

Patients will be screened for eligibility and after eligibility is confirmed and informed consent obtained, pretreatment labs will be done and patients will be admitted. Patients will begin on prophylactic allopurinol 300 mg po qd. Each day prior to treatment, patients will receive acetaminophen 325 mg po, diphenhydramine 25 mg IV (12.5 mg IV for weight<25 kg), hydrocortisone 100 mg IV (50 mg IV for weight<25 kg), rantidine 50 mg IV (1 mg/kg for weight<50 kg), and normal saline 1 L IV over five hours (20 mL/kg for weight<50 kg).

DT2219ARL will be administered into a free-flowing IV over a period of 4 hour QOD×4. Vital signs including blood pressure, pulse, temperature, respirations, and pulse oximetry will be measured every 15-30 minutes for one hour and then hourly for 5 hours and then q 4-8 hours while hospitalized. Patients will be closely monitored for toxicities. Careful I/O will be measured. Additional blood will be collected pretreatment and every 2-3 days for 1 week and then on days 15 and 28 for anti-DT2219ARL and DT2219ARL levels. Blood counts and chemistries will be measured every 2-3 days for 1 week and at days 15 and 28. Supportive measures will include acetaminophen for fevers, meperidine for chills, anti-emetics for nausea and vomiting, normal saline or furosemide to maintain fluid balance/blood pressure/pulmonary function, electrolyte replacement, albumin to maintain serum albumin at 3 g/dL or greater. Anaphylactoid reactions will be treated with 100 mg methylprednisolone IV, diphenhydramine 25 mg IV, or 0.3 cc epinephrine (1:1000) IV and transfer to an ICU setting for monitoring. One cycle of treatment will be given.

The selection of the starting dose for this trial is based on the two species toxicology and prior Phase I trials using diphtheria toxins and recombinant chain ITs described in an earlier section (Vallera et al., 2005). The DT2219ARL starting dose is 0.5 µg/kg/d (1/400th the MTD in rats and rabbits) for patient #1. Dose will be escalated to 1.25 µg/kg/d for patient #2 and 2.5 µg/kg/d for patient #3. The lower doses in single patient cohorts are to identify the risk of capillary leak syndrome toxicities prior to expansion into the higher dose cohorts. These patients are to be treated sequentially, where dosing of the next higher cohort may proceed after completion of the first dosing cycle. A clinical monitoring plan to identify capillary leak syndrome will include evidence of orthostatic hypotension unresponsive to two normal saline boluses or serum albumin <3 g/dL unresponsive to a single 0.5 g/kg albumin infusion. In addition, any drug-related grade 2 toxicity will necessitate expansion to a 3 patient cohort and subsequent dose escalation by 33%. If no drug-related grade 2 toxicity is observed in the first three patients, subsequent dose escalation will be by 100% until evidence of biological activity (grade 2 drug related toxicity) is observed. At that point, dose escalation will be decreased to about 35% increments. If signs of marrow recovery are observed prior to the second week of observation and/or signs of drug-related toxicity have resolved to less than grade 2, additional patients could be added to the cohorts at an earlier time point. No patient will be entered on an escalating dosage level until at least 3 patients have been treated at the previous level and observed for toxicity for at least 3 weeks after the last dose of treatment.

half step escalation (about 17%) will be added to more carefully define the MTD. Responses will be based on response criteria for therapeutic trials of leukemia with clearance of marrow and peripheral blasts and recovery of normal hematopoiesis (Pui and Evans, 2006) or by RECIST criteria for lymphomas (Cheson, 2008).

Correlative studies include the evaluation of response and toxicity in relation to pre-treatment leukemia burden, prior treatments, patient age, sex, leukemia cytogenetics, leukemia and lymphoma CD19 and CD22 antigen densities, PK and antibody levels.

Post-treatment assessment will include bone marrow as appropriate for ALL leukemia and lymphoma assessment, PET CT for lymphoma assessment, cardiac ejection fraction if appropriate, blood counts and chemistries.

Table 3 is description of the patients that have been treated with FDA IND-Approved DT2219ARL. Patients were all in cancer relapse and treated intravenously every-other-day for a total of 4 treatments (QOD×4). Study is incomplete and still accruing patients. Patients according to the approved protocol were ALL or CLL (Ages 20-71) and positive for either CD19 or CD22. Four dose levels have now been completed: 0.5 ug/kg, 1.25 ug/kg, 2.5 ug/kg, and 5 ug/kg. Generally, the findings are the same at all of these low dose levels in all 7 patients. The drug is safe at these low doses since bloodwork and enzymes (not shown) showed no evidence of toxicity. There have been no responses, a finding that correlates with the pk data showing that no drug was in the serum (not shown). It is safe to continue with the phase 1 dose escalation.

TABLE 3

Completion Status of Phase I Study of DT2219ARL (IND# 100780)

| Pt. # | Facility | Age | Gen. | Race | Diagnosis | Disease Status prior to Therapy | Dosage mcg/kg | # of doses received | Completion Status | Response | Pre-TreatBlast % | CD 19 | CD 22 |
|---|---|---|---|---|---|---|---|---|---|---|---|---|---|
| 01 | S&W | 64 | M | White | CLL | Fludarabine Refractory | 0.5 | 4 | Off Study- (Day 28) | Disease Progression | 1 | 58 | 1 |
| 02 | S&W | 71 | M | White | CLL | Fludarabine Refractory | 1.25 | 4 | Off Study- (Day 15) | Disease Progression | — | 99 | 1 |
| 03 | MDACC | 23 | M | Hisp | ALL | Relapsed | 2.5 | 4 | Off Study- (Day 9) | Disease Progression | 91 | 93 | 97 |
| 04 | MDACC | 20 | M | Hisp | ALL | Relapsed | 5.0 | 4 | Off study (Day 8) | No response | 97 | 100 | 64 |
| 05 | MDACC | 32 | F | Hisp | ALL | Relapsed | 5.0 | 4 | Off study (Day 8) | No response | 76 | — | 79 |
| 06 | MDACC | 42 | F | White | ALL | Relapsed | 5.0 | 4 | Off study (Day 15) | No response | 95 | 95 | — |
| 07 | S&W | 11 | F | White | ALL | Relapsed/Refractory | 5.0 | 2 | Off study (Day 5) | No response | 97 | 86 | 5 |

Dose-limiting toxicity (DLT) is defined as any drug-related grade 3 or higher toxicity. Dose levels will be escalated in cohorts of three patients as long as no drug-related non-hematologic toxicity >grade 3 is observed and marrow recovery is sufficiently rapid. If one patient is observed to suffer >grade 3 drug-related toxicity, the cohort will be expanded. If not more than one patient in the expanded cohort of six patients experience drug-related DLT, dose escalation will resume. If two patients enrolled at the same dose level in a cohort of up to six patients experience drug-related DLT, the MTD has been exceeded, and dose escalations will cease. The next lower dose level will be considered the MTD and three additional patients treated at the newly defined MTD level to determine an accurate toxicity profile. If no patients in the expanded cohort at the lower MTD experience DLT, a one- All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,472,509
U.S. Pat. No. 4,472,509
U.S. Pat. No. 5,021,236
U.S. Pat. No. 5,091,513
U.S. Pat. No. 5,401,511
U.S. Pat. No. 5,603,872
U.S. Pat. No. 5,889,155
U.S. Patent Publn. 2005/0214860
Alderson et al., *Clin. Cancer Res.*, 15(3):832-9, 2009.
Anderson et al., *Blood*, 63:1424-33, 1984.
Arap et al., *Cancer Res.*, 55(6):1351-1354, 1995.
Arap et al., *Science*, 279:377-80, 1998.
Bakhshi et al., *Cell*, 41(3):899-906, 1985.
Batra et al., *Proc. Natl. Acad. Sci. USA*, 89:5867-71, 1992.
Bene, *Immunol. Lett.*, 98: 9-21, 2005.
Chan et al., *Blood*, 86:2732-40, 1995.
Cheson, *Ann. Oncol.*, June; 19 Suppl 4:iv35-8, 2008.
Cleary and Sklar, *Proc. Natl. Acad. Sci. USA*, 82(21):7439-7443, 1985.
Cleary et al., *J. Exp. Med.*, 164(1):315-320, 1986.
Collier, *Bacteriol. Rev.*, 39:54-85, 1975.
Devesa et al., *J. Natl. Cancer Inst.*, 79:701, 1987.
Di Paolo et al., *Clin. Cancer Res.*, 9:2837-48, 2003.
Dorken et al., *Verh Dtsch Gs Path.*, 67:65-69, 1983.
Eliceiri and Cheresh, *Curr. Opin. Cell. Biol.*, 13:563-568, 2001.
Ellerby et al., *Nature Med.*, 5:1032-1038, 1999.
Flavell et al., *Br. J. Cancer*, 72:1373-79, 1995.
Folkman, *In: Cancer: Principles and Practice*, eds. DeVita et al., 3075-3085, Lippincott-Raven, N.Y., 1997.
Foon et al., *Annals Int. Medicine*, 113:525, 1990.
Frankel et al., *Cancer Chemother. Biol. Resp. Modif.*, 20: 301-313, 2002.
Freedman, *Hematol. Oncol. Clin. North Am.*, 4:405, 1990.
Ghetie et al., *Blood*, 83:1329-36, 1994.
Gilman's Remington's Pharmaceutical Sciences" 15$^{th}$ ed., pp 1035-1038 and 1570-1580, 1990.
Goodman et al., *Leukemia and Lymphoma*, 22:1, 1996.
Goulet et al., *Blood*, 90:2364-75, 1997.
Herrera et al., *Leukemia*, 17:334-8, 2003.
Ho et al., *J. Biol. Chem.*, 280:607-17, 2005.
Hu et al, *Cancer Res.*, 56:3055-3061, 1996.
Kerr et al., *Br. J. Cancer*, 26(4):239-257, 1972.
Kipriyanov et al., *J. Immunol. Methods*, 196:51-62, 1996.
Klein et al., *Cancer Res.*, 28:1300-10, 1968.
Kreitman et al., *J. Clin. Oncol.*, 23:6719-29, 2005.
Kreitman, *Expert Opin. Biol. Ther.*, 2:785-91, 2002.
List, *Leukemia*, 10:937-942, 1996.
Menard et al., *Oncogene*, 22:6570-78, 2003.
Messmann et al., *Clin. Cancer Res.*, 6:1302-13, 2000.
Morikawa et al., *Int. J. Cancer*, 21:166-70, 1978.
Okamoto et al., *Proc. Natl. Acad. Sci. USA*, 91(23):11045-11049, 1994.
Onda et al., *Proc. Natl. Acad. Sci. USA.*, 105(32):11311-6, 2008.
Oppenheimer and Bodley, *J. Biol. Chem.*, 256:8579-81, 1981.
Physicians Desk Reference
Pui and Evans, *New England J. Med.*, 354: 166-178, 2006.
Pulvertaft, *Lancet.*, 1:238-240, 1964.
Remington's Pharmaceutical Sciences, 15$^{th}$ ed., 33:624-652, Mack Publishing Company, Easton, Pa., 1980.
Salvatore et al., *Clin. Cancer Res.*, 8:995-1002, 2002.
Stish et al., *Clin. Cancer Res.*, 13:3058-67, 2007a.
Stish et al., *Clin. Cancer Res.*, 13:6486-93, 2007b.
Stish et al., *J. Neurooncol.*, 87:51-61, 2008.
Stone et al., *Blood*, 88:1188-97, 1996.
The Pharmacology of Monoclonal Antibodies, Rosenburg and Moore (Eds.), Springer-Verlag, N.Y., 113:269-315, 1994.
Todhunter et al., *Protein Eng. Des. Sel.*, 17:157-64, 2004.
Tsujimoto and Croce, *Proc. Natl. Acad. Sci. USA*, 83(14): 5214-5218, 1986.
Tsujimoto et al., *Nature*, 315:340-343, 1985.
Uckun et al., *J. Exp. Med.*, 163:347-68, 1986.
Vallera et al., *Blood*, 88:2342-53, 1996.
Vallera et al., *Clin. Cancer Res.*, 11:3879-88, 2005.
Vallera et al., *Gut.*, 57:634-41, 2008.
Vallera et al., *Leukemia Res.*, 29:331-41, 2005.
Williams et al., *J. Biol. Chem.*, 265:11885-89, 1990.
Yamaizumi et al., *Cell*, 15:245-50, 1978.

---

The invention claimed is:

1. A conjugate comprising a cytotoxic agent conjugated to a targeting moiety, the targeting moiety comprising: at least a first antigen-binding fragment that binds a first antigen and a second antigen-binding fragment that binds a second antigen, wherein the first or second antigen-binding fragment is CD19 or CD22 and wherein the conjugate has the amino acid sequence as set forth in SEQ ID NO:1.

2. The conjugate of claim 1, wherein said conjugate is a fusion protein.

3. The conjugate of claim 1, wherein said cytotoxic agent is diphtheria toxin or functional fragments thereof.

4. The conjugate of claim 1, wherein said cytotoxic agent comprises the amino terminal 390 amino acids of diphtheria toxin.

5. The conjugate of claim 1, in a pharmaceutically acceptable carrier.

6. A pharmaceutical composition, comprising the conjugate of claim 1.

7. A conjugate comprising an amino acid sequence as set forth in SEQ ID NO:1.

8. A method of treating a human patient having lymphoma or a B-cell malignancy, comprising administering to the patient the conjugate of claim 1.

9. The method of claim 8, wherein said B-cell malignancy is acute lymphoblastic leukemia (ALL).

10. The method of claim 8, further comprising treating said subject with chemotherapy, radiotherapy, surgery, immunotherapy, hormone therapy or gene therapy in conjunction with, prior to or after administering the conjugate of claim 1.

11. A nucleic acid molecule comprising a sequence encoding the conjugate of claim 1.

12. An expression vector comprising the nucleic acid molecule of claim 11.

13. The method of claim 10, wherein the chemotherapy is selected from the group consisting of cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant thereof and combinations thereof.

* * * * *

SEQUENCE LISTING

<160> NUMBER OF SEQ ID NOS: 14

<210> SEQ ID NO 1
<211> LENGTH: 904
<212> TYPE: PRT
<213> ORGANISM: Artificial Sequence
<220> FEATURE:
<223> OTHER INFORMATION: Synthetic peptide

<400> SEQUENCE: 1

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp

```
                  35                  40                  45
Asp Asp Trp Lys Gly Phe Tyr Ser Thr Asp Asn Lys Tyr Asp Ala Ala
 50                  55                  60
Gly Tyr Ser Val Asp Asn Glu Asn Pro Leu Ser Gly Lys Ala Gly Gly
 65                  70                  75                  80
Val Val Lys Val Thr Tyr Pro Gly Leu Thr Lys Val Leu Ala Leu Lys
                     85                  90                  95
Val Asp Asn Ala Glu Thr Ile Lys Lys Glu Leu Gly Leu Ser Leu Thr
                100                 105                 110
Glu Pro Leu Met Glu Gln Val Gly Thr Glu Glu Phe Ile Lys Arg Phe
                115                 120                 125
Gly Asp Gly Ala Ser Arg Val Val Leu Ser Leu Pro Phe Ala Glu Gly
                130                 135                 140
Ser Ser Ser Val Glu Tyr Ile Asn Asn Trp Glu Gln Ala Lys Ala Leu
145                 150                 155                 160
Ser Val Glu Leu Glu Ile Asn Phe Glu Thr Arg Gly Lys Arg Gly Gln
                    165                 170                 175
Asp Ala Met Tyr Glu Tyr Met Ala Gln Ala Cys Ala Gly Asn Arg Val
                180                 185                 190
Arg Arg Ser Val Gly Ser Ser Leu Ser Cys Ile Asn Leu Asp Trp Asp
                195                 200                 205
Val Ile Arg Asp Lys Thr Lys Thr Lys Ile Glu Ser Leu Lys Glu His
                210                 215                 220
Gly Pro Ile Lys Asn Lys Met Ser Glu Ser Pro Asn Lys Thr Val Ser
225                 230                 235                 240
Glu Glu Lys Ala Lys Gln Tyr Leu Glu Glu Phe His Gln Thr Ala Leu
                    245                 250                 255
Glu His Pro Glu Leu Ser Glu Leu Lys Thr Val Thr Gly Thr Asn Pro
                260                 265                 270
Val Phe Ala Gly Ala Asn Tyr Ala Ala Trp Ala Val Asn Val Ala Gln
                275                 280                 285
Val Ile Asp Ser Glu Thr Ala Asp Asn Leu Glu Lys Thr Thr Ala Ala
                290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                    325                 330                 335
Ser Ser Leu Met Val Ala Gln Ala Ile Pro Leu Val Gly Glu Leu Val
                340                 345                 350
Asp Ile Gly Phe Ala Ala Tyr Asn Phe Val Glu Ser Ile Ile Asn Leu
                355                 360                 365
Phe Gln Val Val His Asn Ser Tyr Asn Arg Pro Ala Tyr Ser Pro Gly
                370                 375                 380
His Lys Thr Gln Pro Phe Glu Ala Ser Gly Gly Pro Glu Asp Ile Gln
385                 390                 395                 400
Met Thr Gln Thr Thr Ser Ser Leu Ser Ala Ser Leu Gly Asp Arg Val
                    405                 410                 415
Thr Ile Ser Cys Arg Ala Ser Gln Asp Ile Ser Asn Tyr Leu Asn Trp
                420                 425                 430
Tyr Gln Gln Lys Pro Asp Gly Thr Val Lys Leu Leu Ile Tyr Tyr Thr
                435                 440                 445
Ser Ile Leu His Ser Gly Val Pro Ser Arg Phe Ser Gly Ser Gly Ser
450                 455                 460
```

```
Gly Thr Asp Tyr Ser Leu Thr Ile Ser Asn Leu Glu Gln Glu Asp Phe
465                 470                 475                 480

Ala Thr Tyr Phe Cys Gln Gln Gly Asn Thr Leu Pro Trp Thr Phe Gly
            485                 490                 495

Gly Gly Thr Lys Leu Glu Ile Lys Gly Ser Thr Ser Gly Ser Gly Lys
        500                 505                 510

Pro Gly Ser Gly Glu Gly Ser Thr Lys Gly Glu Val Gln Leu Val Glu
        515                 520                 525

Ser Gly Gly Gly Leu Val Lys Pro Gly Gly Ser Leu Lys Leu Ser Cys
    530                 535                 540

Ala Ala Ser Gly Phe Ala Phe Ser Ile Tyr Asp Met Ser Trp Val Arg
545                 550                 555                 560

Gln Thr Pro Glu Lys Arg Leu Glu Trp Val Ala Tyr Ile Ser Ser Gly
                565                 570                 575

Gly Gly Thr Thr Tyr Tyr Pro Asp Thr Val Lys Gly Arg Phe Thr Ile
            580                 585                 590

Ser Arg Asp Asn Ala Lys Asn Thr Leu Tyr Leu Gln Met Ser Ser Leu
        595                 600                 605

Lys Ser Glu Asp Thr Ala Met Tyr Tyr Cys Ala Arg His Ser Gly Tyr
610                 615                 620

Gly Thr His Trp Gly Val Leu Phe Ala Tyr Trp Gly Gln Gly Thr Leu
625                 630                 635                 640

Val Thr Val Ser Ala Gly Gly Gly Ser Asp Ile Leu Leu Thr Gln
                645                 650                 655

Thr Pro Ala Ser Leu Ala Val Ser Leu Gly Gln Arg Ala Thr Ile Ser
                660                 665                 670

Cys Lys Ala Ser Gln Ser Val Asp Tyr Asp Gly Asp Ser Tyr Leu Asn
            675                 680                 685

Trp Tyr Gln Gln Ile Pro Gly Gln Pro Pro Lys Leu Leu Ile Tyr Asp
    690                 695                 700

Ala Ser Asn Leu Val Ser Gly Ile Pro Pro Arg Phe Ser Gly Ser Gly
705                 710                 715                 720

Ser Gly Thr Asp Phe Thr Leu Asn Ile His Pro Val Glu Lys Val Asp
                725                 730                 735

Ala Ala Thr Tyr His Cys Gln Gln Ser Thr Glu Asp Pro Trp Thr Phe
                740                 745                 750

Gly Gly Gly Thr Lys Leu Glu Ile Lys Arg Gly Ser Thr Ser Gly Ser
            755                 760                 765

Gly Lys Pro Gly Ser Gly Glu Gly Ser Thr Lys Gly Gln Val Gln Leu
        770                 775                 780

Gln Gln Ser Gly Ala Glu Leu Val Arg Pro Gly Ser Ser Val Lys Ile
785                 790                 795                 800

Ser Cys Lys Ala Ser Gly Tyr Ala Phe Ser Ser Tyr Trp Met Asn Trp
                805                 810                 815

Val Lys Gln Arg Pro Gly Gln Gly Leu Glu Trp Ile Gly Gln Ile Trp
                820                 825                 830

Pro Gly Asp Gly Asp Thr Asn Tyr Asn Gly Lys Phe Lys Gly Lys Ala
            835                 840                 845

Thr Leu Thr Ala Asp Glu Ser Ser Thr Ala Tyr Met Gln Leu Ser
    850                 855                 860

Ser Leu Ala Ser Glu Asp Ser Ala Val Tyr Phe Cys Ala Arg Arg Glu
865                 870                 875                 880
```

```
          Thr Thr Thr Val Gly Arg Tyr Tyr Tyr Ala Met Asp Tyr Trp Gly Gln
                      885                 890                 895

Gly Thr Ser Val Thr Val Ser Ser
                      900

<210> SEQ ID NO 2
<211> LENGTH: 2715
<212> TYPE: DNA
<213> ORGANISM: Artificial Sequence
<220> FEATURE:
<223> OTHER INFORMATION: Synthetic primer

<400> SEQUENCE: 2
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta agaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tcaggaaat cgtgtcaggc gatcagtagg tagctcattg     600
```

```
tcatgcataa atcttgattg ggatgtcata agggataaaa ctaagacaaa gatagagtct     660
ttgaaagagc atggccctat caaaaataaa atgagcgaaa gtcccaataa aacagtatct     720
gaggaaaaag ctaaacaata cctagaagaa tttcatcaaa cggcattaga gcatcctgaa     780
ttgtcagaac ttaaaaccgt tactgggacc aatcctgtat tcgctggggc taactatgcg     840
gcgtgggcag taaacgttgc gcaagttatc gatagcgaaa cagctgataa tttggaaaag     900
acaactgctg ctctttcgat acttcctggt atcggtagcg taatgggcat gcagacggt     960 gccgttcacc acaatacaga agagatagtg cacaatcaa tagctttatc gtctttaatg    1020
gttgctcaag ctattccatt ggtaggagag ctagttgata ttggtttcgc tgcatataat    1080
tttgtagaga gtattatcaa tttatttcaa gtagttcata attcgtataa tcgtcccgcg    1140
tattctccgg ggcataaaac gcaaccattt gaagcttccg gaggtcccga ggatattcaa    1200
atgactcaaa ctacttcttc tttgtctgct tctttgggtg atagagttac tatttcttgt    1260
agagcttctc aagatatttc taactacttg aactggtacc aacaaaagcc agatggtact    1320
gttaagttgt tgatttacta cacttccatt ttgcattctg tgttccatc tagattctct    1380 ggttctggtt ctggtactga ttactctttg actatttcta cttggaaca gaagatttc    1440 gctacttact ctgtcaaca aggtaatact ttgccatgga ctttcggtgg tggtactaag    1500
ttggaaatta agggtagcac ctctggctcc ggaaaaccgg gaagcggtga agggtccacc    1560
aagggtgaag ttcaattggt tgaatctggt ggtggtttgg ttaagccagg tggttctttg    1620
aagttgtctt gtgctgcttc tggtttcgct ttctctattt acgatatgtc ttgggttaga    1680
caaactccag aaaagagatt ggaatgggtt gcttacattt cttctggtgg tggtactact    1740
tactacccag atactgttaa gggtagattc actatttcta gagataacgc taagaacact    1800
ttgtacctgc aaatgtcttc tctgaagtct gaagataccg ctatgtacta ctgtgctaga    1860
cattccggtt acggtaccca ctgggggtgtt ttgttcgctt actgggtca aggtacttg    1920
```

```
gttactgttt ctgctggtgg cggtggatcc gatatcttgc tcacccaaac tccagcttct    1980
ttggctgtgt ctctagggca gagggccacc atctcctgca aggccagcca aagtgttgat    2040
tatgatggtg atagttattt gaactggtac caacagattc caggacagcc acccaaactc    2100
ctcatctatg atgcatccaa tctagtttct gggattccac ccaggtttag tggcagtggg    2160
tctgggacag acttcaccct caacatccat cctgtggaga aggtggatgc tgcaacctat    2220
cactgtcagc aaagtactga agatccgtgg acgttcggtg gaggcaccaa gctgaaatc     2280 aaacggggta gcacctctgg ctccggaaaa ccgggaagcg gtgaagggtc caccaagggt    2340
caggtgcagc tgcagcagtc tggggctgag ctggtgaggc ctgggtcctc agtgaagatt    2400
tcctgcaagg cttctggcta tgcattcagt agctactgga tgaactgggt gaagcagagg    2460
cctggacagg gtcttgagtg gattggacag atttggcctg agatggtga tactaactac    2520 aatggaaagt tcaagggtaa agccactctg actgcagacg aatcctccag cacagcctac    2580
atgcaactca gcagcctagc atctgaggac tctgcggtct atttctgtgc aagacgggag    2640
actacgacgg taggccgtta ttactatgct atggactact ggggtcaagg aacctcagtc    2700
accgtctcct catag                                                    2715

<210> SEQ ID NO 3
<211> LENGTH: 390
<212> TYPE: PRT
<213> ORGANISM: Artificial Sequence
<220> FEATURE:
<223> OTHER INFORMATION: Synthetic peptide

<400> SEQUENCE: 3

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
```

```
Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
            245                 250                 255

Glu His Pro Glu Leu Ser Glu Leu Lys Thr Val Thr Gly Thr Asn Pro
        260                 265                 270

Val Phe Ala Gly Ala Asn Tyr Ala Ala Trp Ala Val Asn Val Ala Gln
    275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
            325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Phe
385             390

<210> SEQ ID NO 4
<211> LENGTH: 1170
<212> TYPE: DNA
<213> ORGANISM: Artificial Sequence
<220> FEATURE:
<223> OTHER INFORMATION: Synthetic primer

<400> SEQUENCE: 4
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcataa atcttgattg ggatgtcata agggataaaa ctaagacaaa gatagagtct     660
ttgaaagagc atggccctat caaaaataaa atgagcgaaa gtcccaataa aacagtatct     720
gaggaaaaag ctaaacaata cctagaagaa tttcatcaaa cggcattaga gcatcctgaa     780
ttgtcagaac ttaaaccgt tactgggacc aatcctgtat cgctggggc taactatgcg     840 gcgtgggcag taacgttgc gcaagttatc gatagcgaaa cagctgataa tttggaaaag     900
acaactgctg ctcttttcgat acttcctggt atcggtagcg taatgggcat tgcagacggt     960
gccgttcacc acaatacaga agagatagtg cacaatcaa tagctttatc gtctttaatg    1020
```

```
gttgctcaag ctattccatt ggtaggagag ctagttgata ttggtttcgc tgcatataat    1080
tttgtagaga gtattatcaa tttatttcaa gtagttcata attcgtataa tcgtcccgcg    1140
tattctccgg ggcataaaac gcaaccattt                                     1170
```

```
<210> SEQ ID NO 5
<211> LENGTH: 362
<212> TYPE: PRT
<213> ORGANISM: Artificial Sequence
<220> FEATURE:
<223> OTHER INFORMATION: Synthetic peptide

<400> SEQUENCE: 5
```

| Pro | Glu | Gly | Gly | Ser | Leu | Ala | Ala | Leu | Thr | Ala | His | Gln | Ala | Cys | His |
|---|---|---|---|---|---|---|---|---|---|---|---|---|---|---|---|
| 1 | | | | 5 | | | | | 10 | | | | | 15 | |

| Leu | Pro | Leu | Glu | Thr | Phe | Thr | Arg | His | Arg | Gln | Pro | Arg | Gly | Trp | Glu |
|---|---|---|---|---|---|---|---|---|---|---|---|---|---|---|---|
| | | | 20 | | | | | 25 | | | | | 30 | | |

| Gln | Leu | Glu | Gln | Cys | Gly | Tyr | Pro | Val | Gln | Arg | Leu | Val | Ala | Leu | Tyr |
| | | 35 | | | | | 40 | | | | | 45 | | | |

| Leu | Ala | Ala | Arg | Leu | Ser | Trp | Asn | Gln | Val | Asp | Gln | Val | Ile | Arg | Asn |
| 50 | | | | | 55 | | | | | 60 | | | | | |

| Ala | Leu | Ala | Ser | Pro | Gly | Ser | Gly | Gly | Asp | Leu | Gly | Glu | Ala | Ile | Arg |
| 65 | | | | | 70 | | | | | 75 | | | | | 80 |

| Glu | Gln | Pro | Glu | Gln | Ala | Arg | Leu | Ala | Leu | Thr | Leu | Ala | Ala | Ala | Glu |
| | | | | 85 | | | | | 90 | | | | | 95 | |

| Ser | Glu | Arg | Phe | Val | Arg | Gln | Gly | Thr | Gly | Asn | Asp | Glu | Ala | Gly | Ala |
| | | | 100 | | | | | 105 | | | | | 110 | | |

| Ala | Asn | Ala | Asp | Val | Val | Ser | Leu | Thr | Cys | Pro | Val | Ala | Ala | Gly | Glu |
| | | 115 | | | | | 120 | | | | | 125 | | | |

| Cys | Ala | Gly | Pro | Ala | Asp | Ser | Gly | Asp | Ala | Leu | Leu | Glu | Arg | Asn | Tyr |
| 130 | | | | | 135 | | | | | 140 | | | | | |

| Pro | Thr | Gly | Ala | Glu | Phe | Leu | Gly | Asp | Gly | Asp | Val | Ser | Phe | Ser |
| 145 | | | | | 150 | | | | | 155 | | | | | 160 |

| Thr | Arg | Gly | Thr | Gln | Asn | Trp | Thr | Val | Glu | Arg | Leu | Leu | Gln | Ala | His |
| | | | 165 | | | | | 170 | | | | | 175 | | |

| Arg | Gln | Leu | Glu | Glu | Arg | Gly | Tyr | Val | Phe | Val | Gly | Tyr | His | Gly | Thr |
| | | | 180 | | | | | 185 | | | | | 190 | | |

| Phe | Leu | Glu | Ala | Ala | Gln | Ser | Ile | Val | Phe | Gly | Gly | Val | Arg | Ala | Arg |
| | | 195 | | | | | 200 | | | | | 205 | | | |

| Ser | Gln | Asp | Leu | Asp | Ala | Ile | Trp | Arg | Gly | Phe | Tyr | Ile | Ala | Gly | Asp |
| 210 | | | | | 215 | | | | | 220 | | | | | |

| Pro | Ala | Leu | Ala | Tyr | Gly | Tyr | Ala | Gln | Asp | Gln | Glu | Pro | Asp | Ala | Arg |
| 225 | | | | | 230 | | | | | 235 | | | | | 240 |

| Gly | Arg | Ile | Arg | Asn | Gly | Ala | Leu | Leu | Arg | Val | Tyr | Val | Pro | Arg | Ser |
| | | | | 245 | | | | | 250 | | | | | 255 | |

| Ser | Leu | Pro | Gly | Phe | Tyr | Arg | Thr | Ser | Leu | Thr | Leu | Ala | Ala | Pro | Glu |
| | | | 260 | | | | | 265 | | | | | 270 | | |

| Ala | Ala | Gly | Glu | Val | Glu | Arg | Leu | Ile | Gly | His | Pro | Leu | Pro | Leu | Arg |
| | | 275 | | | | | 280 | | | | | 285 | | | |

| Leu | Asp | Ala | Ile | Thr | Gly | Pro | Glu | Glu | Glu | Gly | Gly | Arg | Leu | Glu | Thr |
| | | 290 | | | | | 295 | | | | | 300 | | | |

| Ile | Leu | Gly | Trp | Pro | Leu | Ala | Glu | Arg | Thr | Val | Val | Ile | Pro | Ser | Ala |
| 305 | | | | | 310 | | | | | 315 | | | | | 320 |

| Ile | Pro | Thr | Asp | Pro | Arg | Asn | Val | Gly | Gly | Asp | Leu | Asp | Pro | Ser | Ser |
| | | | | 325 | | | | | 330 | | | | | 335 | |

```
Ile Pro Asp Lys Glu Gln Ala Ile Ser Ala Leu Pro Asp Tyr Ala Ser
                340                 345                 350

Gln Pro Gly Lys Pro Pro Lys Asp Glu Leu
        355                 360
```

<210> SEQ ID NO 6
<211> LENGTH: 1089
<212> TYPE: DNA
<213> ORGANISM: Artificial Sequence
<220> FEATURE:
<223> OTHER INFORMATION: Synthetic primer

<400> SEQUENCE: 6

| | | |
|---|---|---|
| cccgagggcg gcagcctggc cgcgctgacc gcgcaccagg cttgccacct gccgctggag | 60 |
| actttcaccc gtcatcgcca gccgcgcggc tgggaacaac tggagcagtg cggctatccg | 120 |
| gtgcagcggc tggtcgccct ctacctggcg gcgcggctgt cgtggaacca ggtcgaccag | 180 |
| gtgatccgca acgccctggc cagccccggc agcggcggcg acctgggcga agcgatccgc | 240 |
| gagcagccgg agcaggcccg tctggccctg accctggccg ccgccgagag cgagcgcttc | 300 |
| gtccggcagg gcaccggcaa cgacgaggcc ggcgcggcca acgccgacgt ggtgagcctg | 360 |
| acctgccgg tcgccgccgg tgaatgcgcg ggcccgggcg acagcggcga cgccctgctg | 420 |
| gagcgcaact atcccactgg cgcggagttc ctcggcgacg gcggcgacgt cagcttcagc | 480 |
| acccgcggca cgcagaactg gacggtggag cggctgctcc aggcgcaccg ccaactggag | 540 |
| gagcgcggct atgtgttcgt cggctaccac ggcaccttcc tcgaagcggc gcaaagcatc | 600 |
| gtcttcggcg gggtgcgcgc gcgcagccag gacctcgacg cgatctggcg cggttttctat | 660 |
| atcgccggcg atccggcgct ggcctacggc tacgcccagg accaggaacc cgacgcacgc | 720 |
| ggccggatcc gcaacggtgc cctgctgcgg gtctatgtgc cgcgctcgag cctgccgggc | 780 |
| ttctaccgca ccagcctgac cctggccgcg ccggaggcgg cgggcgaggt cgaacggctg | 840 |
| atcggccatc cgctgccgct gcgcctggac gccatcaccg gccccgagga ggaaggcggg | 900 |
| cgcctggaga ccattctcgg ctggccgctg gccgagcgca ccgtggtgat tccctcggcg | 960 |
| atccccaccg acccgcgcaa cgtcggcggc gacctcgacc cgtccagcat ccccgacaag | 1020 |
| gaacaggcga tcagcgccct gccggactac gccagccagc ccggcaaacc gccgaaggac | 1080 |
| gagctatga | 1089 |

<210> SEQ ID NO 7
<211> LENGTH: 877
<212> TYPE: PRT
<213> ORGANISM: Artificial Sequence
<220> FEATURE:
<223> OTHER INFORMATION: Synthetic peptide

<400> SEQUENCE: 7

```
Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Ser Asn
                20                  25                  30

Tyr Leu Asn Trp Tyr Gln Gln Lys Pro Asp Gly Thr Val Lys Leu Leu
            35                  40                  45

Ile Tyr Tyr Thr Ser Ile Leu His Ser Gly Val Pro Ser Arg Phe Ser
    50                  55                  60

Gly Ser Gly Ser Gly Thr Asp Tyr Ser Leu Thr Ile Ser Asn Leu Glu
65                  70                  75                  80
```

```
Gln Glu Asp Phe Ala Thr Tyr Phe Cys Gln Gln Gly Asn Thr Leu Pro
                 85                  90                  95
Trp Thr Phe Gly Gly Gly Thr Lys Leu Glu Ile Lys Gly Ser Thr Ser
            100                 105                 110
Gly Ser Gly Lys Pro Gly Ser Gly Glu Gly Ser Thr Lys Gly Glu Val
        115                 120                 125
Gln Leu Val Glu Ser Gly Gly Leu Val Lys Pro Gly Gly Ser Leu
130                 135                 140
Lys Leu Ser Cys Ala Ala Ser Gly Phe Ala Phe Ser Ile Tyr Asp Met
145                 150                 155                 160
Ser Trp Val Arg Gln Thr Pro Glu Lys Arg Leu Glu Trp Val Ala Tyr
                165                 170                 175
Ile Ser Ser Gly Gly Gly Thr Thr Tyr Tyr Pro Asp Thr Val Lys Gly
            180                 185                 190
Arg Phe Thr Ile Ser Arg Asp Asn Ala Lys Asn Thr Leu Tyr Leu Gln
        195                 200                 205
Met Ser Ser Leu Lys Ser Glu Asp Thr Ala Met Tyr Tyr Cys Ala Arg
    210                 215                 220
His Ser Gly Tyr Gly Thr His Trp Gly Val Leu Phe Ala Tyr Trp Gly
225                 230                 235                 240
Gln Gly Thr Leu Val Thr Val Ser Ala Gly Gly Gly Ser Asp Ile
                245                 250                 255
Leu Leu Thr Gln Thr Pro Ala Ser Leu Ala Val Ser Leu Gly Gln Arg
            260                 265                 270
Ala Thr Ile Ser Cys Lys Ala Ser Gln Ser Val Asp Tyr Asp Gly Asp
        275                 280                 285
Ser Tyr Leu Asn Trp Tyr Gln Gln Ile Pro Gly Gln Pro Pro Lys Leu
    290                 295                 300
Leu Ile Tyr Asp Ala Ser Asn Leu Val Ser Gly Ile Pro Pro Arg Phe
305                 310                 315                 320
Ser Gly Ser Gly Ser Gly Thr Asp Phe Thr Leu Asn Ile His Pro Val
                325                 330                 335
Glu Lys Val Asp Ala Ala Thr Tyr His Cys Gln Gln Ser Thr Glu Asp
            340                 345                 350
Pro Trp Thr Phe Gly Gly Gly Thr Lys Leu Glu Ile Lys Arg Gly Ser
        355                 360                 365
Thr Ser Gly Ser Gly Lys Pro Gly Ser Gly Glu Gly Ser Thr Lys Gly
    370                 375                 380
Gln Val Gln Leu Gln Gln Ser Gly Ala Glu Leu Val Arg Pro Gly Ser
385                 390                 395                 400
Ser Val Lys Ile Ser Cys Lys Ala Ser Gly Tyr Ala Phe Ser Ser Tyr
                405                 410                 415
Trp Met Asn Trp Val Lys Gln Arg Pro Gly Gln Gly Leu Glu Trp Ile
            420                 425                 430
Gly Gln Ile Trp Pro Gly Asp Gly Asp Thr Asn Tyr Asn Gly Lys Phe
        435                 440                 445
Lys Gly Lys Ala Thr Leu Thr Ala Asp Glu Ser Ser Ser Thr Ala Tyr
    450                 455                 460
Met Gln Leu Ser Ser Leu Ala Ser Glu Asp Ser Ala Val Tyr Phe Cys
465                 470                 475                 480
Ala Arg Arg Glu Thr Thr Thr Val Gly Arg Tyr Tyr Tyr Ala Met Asp
                485                 490                 495
Tyr Trp Gly Gln Gly Thr Ser Val Thr Val Ser Ser Glu Ala Ser Gly
```

```
            500                 505                 510
Gly Pro Glu Pro Glu Gly Gly Ser Leu Ala Ala Leu Thr Ala His Gln
            515                 520                 525

Ala Cys His Leu Pro Leu Glu Thr Phe Thr Arg His Arg Gln Pro Arg
            530                 535                 540

Gly Trp Glu Gln Leu Glu Gln Cys Gly Tyr Pro Val Gln Arg Leu Val
545                 550                 555                 560

Ala Leu Tyr Leu Ala Ala Arg Leu Ser Trp Asn Gln Val Asp Gln Val
                565                 570                 575

Ile Ala Asn Ala Leu Ala Ser Pro Gly Ser Gly Asp Leu Gly Glu
            580                 585                 590

Ala Ile Arg Glu Ser Pro Glu Gln Ala Arg Leu Ala Leu Thr Leu Ala
            595                 600                 605

Ala Ala Glu Ser Glu Arg Phe Val Arg Gln Gly Thr Gly Asn Asp Glu
            610                 615                 620

Ala Gly Ala Ala Asn Ala Asp Val Val Ser Leu Thr Cys Pro Val Ala
625                 630                 635                 640

Ala Gly Glu Cys Ala Gly Pro Ala Asp Ser Gly Asp Ala Leu Leu Glu
            645                 650                 655

Arg Asn Tyr Pro Thr Gly Ala Glu Phe Leu Gly Asp Gly Asp Val
            660                 665                 670

Ser Phe Ser Thr Arg Gly Thr Gln Asn Trp Thr Val Glu Arg Leu Leu
            675                 680                 685

Gln Ala His Arg Gln Leu Glu Glu Gly Gly Tyr Val Phe Val Gly Tyr
            690                 695                 700

His Gly Thr Phe Leu Glu Ala Ala Gln Ser Ile Val Phe Gly Gly Val
705                 710                 715                 720

Arg Ala Arg Ser Gln Asp Leu Asp Ala Ile Trp Ala Gly Phe Tyr Ile
                725                 730                 735

Ala Gly Asp Pro Ala Leu Ala Tyr Gly Tyr Ala Gln Asp Gln Glu Pro
            740                 745                 750

Asp Ala Ala Gly Arg Ile Arg Asn Gly Ala Leu Leu Arg Val Tyr Val
            755                 760                 765

Pro Arg Ser Ser Leu Pro Gly Phe Tyr Ala Thr Ser Leu Thr Leu Ala
770                 775                 780

Ala Pro Glu Ala Ala Gly Glu Val Glu Arg Leu Ile Gly His Pro Leu
785                 790                 795                 800

Pro Leu Arg Leu Asp Ala Ile Thr Gly Pro Glu Glu Ser Gly Gly Arg
                805                 810                 815

Leu Glu Thr Ile Leu Gly Trp Pro Leu Ala Glu Arg Thr Val Val Ile
            820                 825                 830

Pro Ser Ala Ile Pro Thr Asp Pro Arg Asn Val Gly Gly Asp Leu Asp
            835                 840                 845

Pro Ser Ser Ile Pro Asp Ser Glu Gln Ala Ile Ser Ala Leu Pro Asp
850                 855                 860

Tyr Ala Ser Gln Pro Gly Lys Pro Lys Asp Glu Leu
865                 870                 875

<210> SEQ ID NO 8
<211> LENGTH: 2634
<212> TYPE: DNA
<213> ORGANISM: Artificial Sequence
<220> FEATURE:
<223> OTHER INFORMATION: Synthetic primer
```

```
<400> SEQUENCE: 8
atggatattc aaatgactca aactacttct tctttgtctg cttctttggg tgatagagtt      60
actatttctt gtagagcttc tcaagatatt tctaactact tgaactggta ccaacaaaag     120
ccagatggta ctgttaagtt gttgatttac tacacttcca ttttgcattc tggtgttcca     180
tctagattct ctggttctgg ttctggtact gattactctt tgactatttc taacttggaa     240
caagaagatt tcgctactta cttctgtcaa caaggtaata ctttgccttg gactttcggt     300
ggtggtacta agttggaaat taagggtagc acctctggct ccggaaaacc gggaagcggt     360
gaagggtcca ccaagggtga agttcaattg gttgaatctg gtggtggttt ggttaagcca     420
ggtggttctt tgaagttgtc ttgtgctgct tctggttttcg ctttctctat ttacgatatg     480
tcttgggtta gacaaactcc agaaaagaga ttggaatggg ttgcttacat ttcttctggt     540
ggtggtacta cttactaccc agatactgtt aagggtagat tcactatttc tagagataac     600
gctaagaaca ctttgtacct gcaaatgtct ctctgaagt ctgaagatac cgctatgtac     660
tactgtgcta gacattccgg ttacggtacc cactgggggtg ttttgttcgc ttactgggggt     720 caaggtactt tggttactgt ttctgctggt ggcggtggat ccgatatctt gctcacccaa     780
actccagctt ctttggctgt gtctctaggg cagagggcca ccatctcctg caaggccagc     840
caaagtgttg attatgatgg tgatagttat ttgaactggt accaacagat tccaggacag     900
ccacccaaac tcctcatcta tgatgcatcc aatctagttt ctgggattcc acccaggttt     960
agtggcagtg ggtctgggac agacttcacc ctcaacatcc atcctgtgga aggtggat     1020 gctgcaacct atcactgtca gcaaagtact gaagatccgt ggacgttcgg tggaggcacc    1080
aagctggaaa tcaaacgggg tagcacctct ggctccggaa aaccgggaag cggtgaaggg    1140
tccaccaagg gtcaggtgca gctgcagcag tctggggctg agctggtgag gcctgggtcc    1200
tcagtgaaga tttcctgcaa ggcttctggc tatgcattca gtagctactg gatgaactgg    1260
gtgaagcaga ggcctggaca gggtcttgag tggattggac agatttggcc tggagatggt    1320
gatactaact acaatggaaa gttcaagggt aaagccactc tgactgcaga cgaatcctcc    1380
agcacagcct acatgcaact cagcagccta gcatctgagg actctgcggt ctatttctgt    1440
gcaagacggg agactacgac ggtaggccgt tattactatg ctatggacta ctggggtcaa    1500
ggaacctcag tcaccgtctc ctcagaagct tccggaggtc ccgagcccga gggcggcagc    1560
ctggccgcgc tgaccgcgca ccaggcttgc cacctgccgc tggagacttt cacccgtcat    1620
cgccagccgc gcggctggga caactggag cagtgcggct atccggtgca gcggctggtc    1680
gccctctacc tggcggcgcg gctgtcgtgg aaccaggtcg accaggtgat cgccaacgcc    1740
ctggccagcc ccggcagcgg cggcgacctg ggcgaagcga tccgcgagtc gccggagcag    1800
gcccgtctgg ccctgacccc tggccgccgcc gagagcgagc gcttcgtccg gcagggcacc    1860
ggcaacgacg aggccggcgc ggccaacgcc gacgtggtga gcctgacctg cccggtcgcc    1920
gccggtgaat gcgcgggccc ggcggacagc ggcgacgccc tgctggagcg caactatccc    1980
actggcgcgg agttcctcgg cgacggcggc gacgtcagct tcagcacccg cggcacgcag    2040
aactggacgg tggagcggct gctccaggcg caccgccaac tggaggaggg aggctatgtg    2100
ttcgtcggct accacggcac cttcctcgaa gcggcgcaaa gcatcgtctt cggcggggtg    2160
cgcgcgcgca gccaggacct cgacgcgatc tgggccggtt tctatatcgc cggcgatccg    2220
gcgctggcct acgctacgc ccaggaccag gaacccgacg cagccggccg gatccgcaac    2280
ggtgccctgc tgcgggtcta tgtgccgcgc tcgagcctgc cggcttcta cgccaccagc    2340
```

```
ctgaccctgg ccgcgccgga ggcggcgggc gaggtcgaac ggctgatcgg ccatccgctg    2400
ccgctgcgcc tggacgccat caccggcccc gaggagtcag gcgggcgcct ggagaccatt    2460
ctcggctggc cgctggccga gcgcaccgtg gtgattccct cggcgatccc caccgacccg    2520
cgcaacgtcg gcggcgacct cgacccgtcc agcatccccg actcggaaca ggcgatcagc    2580
gccctgccgg actacgccag ccagcccggc aaaccgccga aggacgagct atga          2634
```

<210> SEQ ID NO 9
<211> LENGTH: 14
<212> TYPE: PRT
<213> ORGANISM: Artificial Sequence
<220> FEATURE:
<223> OTHER INFORMATION: Synthetic peptide

<400> SEQUENCE: 9

```
Lys Leu Ala Lys Leu Ala Lys Lys Leu Ala Lys Leu Ala Lys
1               5                   10
```

<210> SEQ ID NO 10
<211> LENGTH: 14
<212> TYPE: PRT
<213> ORGANISM: Artificial Sequence
<220> FEATURE:
<223> OTHER INFORMATION: Synthetic peptide

<400> SEQUENCE: 10

```
Lys Leu Ala Lys Lys Leu Ala Lys Leu Ala Lys Lys Leu Ala
1               5                   10
```

<210> SEQ ID NO 11
<211> LENGTH: 14
<212> TYPE: PRT
<213> ORGANISM: Artificial Sequence
<220> FEATURE:
<223> OTHER INFORMATION: Synthetic peptide

<400> SEQUENCE: 11

```
Lys Ala Ala Lys Lys Ala Ala Lys Ala Ala Lys Lys Ala Ala
1               5                   10
```

<210> SEQ ID NO 12
<211> LENGTH: 21
<212> TYPE: PRT
<213> ORGANISM: Artificial Sequence
<220> FEATURE:
<223> OTHER INFORMATION: Synthetic peptide

<400> SEQUENCE: 12

```
Lys Leu Gly Lys Lys Leu Gly Lys Leu Gly Lys Lys Leu Gly Lys Leu
1               5                   10                  15

Gly Lys Lys Leu Gly
            20
```

<210> SEQ ID NO 13
<211> LENGTH: 20
<212> TYPE: PRT
<213> ORGANISM: Artificial Sequence
<220> FEATURE:
<223> OTHER INFORMATION: Synthetic peptide

<400> SEQUENCE: 13

```
Pro Ser Gly Gln Ala Gly Ala Ala Ala Ser Glu Ser Leu Phe Val Ser
1               5                   10                  15
```

```
Asn His Ala Tyr
            20

<210> SEQ ID NO 14
<211> LENGTH: 18
<212> TYPE: PRT
<213> ORGANISM: Artificial Sequence
<220> FEATURE:
<223> OTHER INFORMATION: Synthetic peptide

<400> SEQUENCE: 14

Gly Ser Thr Ser Gly Ser Gly Lys Pro Gly Ser Gly Glu Gly Ser Thr
1               5                   10                  15

Lys Gly
```